US012150862B2

(12) United States Patent
Patel

(10) Patent No.: US 12,150,862 B2
(45) Date of Patent: *Nov. 26, 2024

(54) MINIMALLY INVASIVE POSTERIOR CERVICAL FACET ARTHRODESIS SHIM IMPLANT AND TOOLS THEREFOR

(71) Applicant: Anjali Investments, LLC, Lutherville-Timonium, MD (US)

(72) Inventor: Amit Patel, Lutherville-Timonium, MD (US)

(73) Assignee: Anjali Investments LLC, Timonium, MD (US)

( * ) Notice: Subject to any disclaimer, the term of this patent is extended or adjusted under 35 U.S.C. 154(b) by 40 days.

This patent is subject to a terminal disclaimer.

(21) Appl. No.: 18/158,248

(22) Filed: Jan. 23, 2023

(65) Prior Publication Data

US 2023/0157833 A1    May 25, 2023

Related U.S. Application Data

(62) Division of application No. 16/876,948, filed on May 18, 2020, now Pat. No. 11,583,408.

(60) Provisional application No. 62/849,850, filed on May 18, 2019.

(51) Int. Cl.
*A61F 2/44* (2006.01)
*A61B 17/70* (2006.01)
*A61F 2/30* (2006.01)

(52) U.S. Cl.
CPC ........ *A61F 2/4405* (2013.01); *A61B 17/7062* (2013.01); *A61B 17/7074* (2013.01); *A61F 2/30767* (2013.01); *A61F 2002/30405* (2013.01); *A61F 2002/3093* (2013.01); *A61F 2310/00023* (2013.01); *A61F 2310/00131* (2013.01); *A61F 2310/00796* (2013.01)

(58) Field of Classification Search
CPC ................ A61F 2/4405; A61F 2/30767; A61F 2002/30405; A61F 2002/3093; A61F 2310/00023; A61F 2310/00131; A61F 2310/00796; A61B 17/7062; A61B 17/7074
USPC ...................... 623/17.11–17.16; 606/246–249
See application file for complete search history.

(56) References Cited

U.S. PATENT DOCUMENTS 5,766,251 A * 6/1998 Koshino .................... A61F 2/28
606/246
8,100,972 B1 * 1/2012 Bruffey ................. A61F 2/4465
623/17.11

(Continued)

*Primary Examiner* — Eduardo C Robert
*Assistant Examiner* — Tara Rose E Carter
(74) *Attorney, Agent, or Firm* — Andrew H. Berks

(57) ABSTRACT

The shim-type implant for distraction and fusion of cervical facet joints is provided. The implant has a generally box-like shape with a blunt leading edge that may be centered or offset to the inferior face. The implant may include a graft window for enhanced osseous through-growth after implantation. The implant is coated with hydroxyapatite (HA) and/or tri-calcium phosphate (TCP) to allow for osteoconduction, is porous, and has a roughened surface with serrations on the superior and inferior faces. The implant may be fabricated from a titanium or tantalum alloy. In an embodiment, a set of tools is provided with a chisel and one or tongs and one or more decorticators for inserting the implant.

10 Claims, 16 Drawing Sheets

(56) References Cited

U.S. PATENT DOCUMENTS

| | | | |
|---|---|---|---|
| 2006/0051395 A1* | 3/2006 | Beyer, Jr. | A61P 19/00 |
| | | | 514/21.3 |
| 2006/0110708 A1* | 5/2006 | Faus Badia | A61C 8/0012 |
| | | | 433/173 |
| 2011/0230965 A1* | 9/2011 | Schell | A61B 17/7064 |
| | | | 606/86 A |
| 2013/0012994 A1* | 1/2013 | McCormack | A61F 2/4611 |
| | | | 606/247 |

* cited by examiner

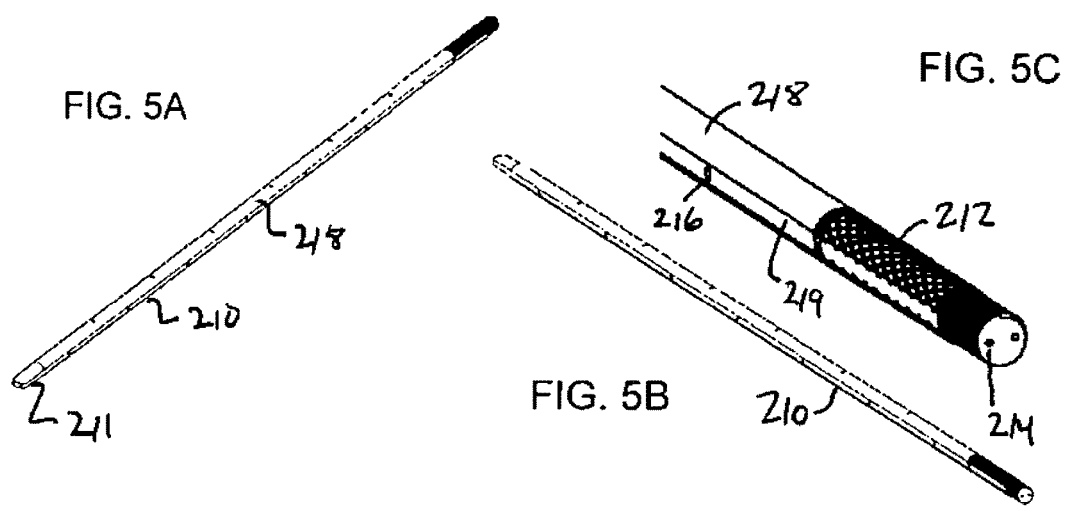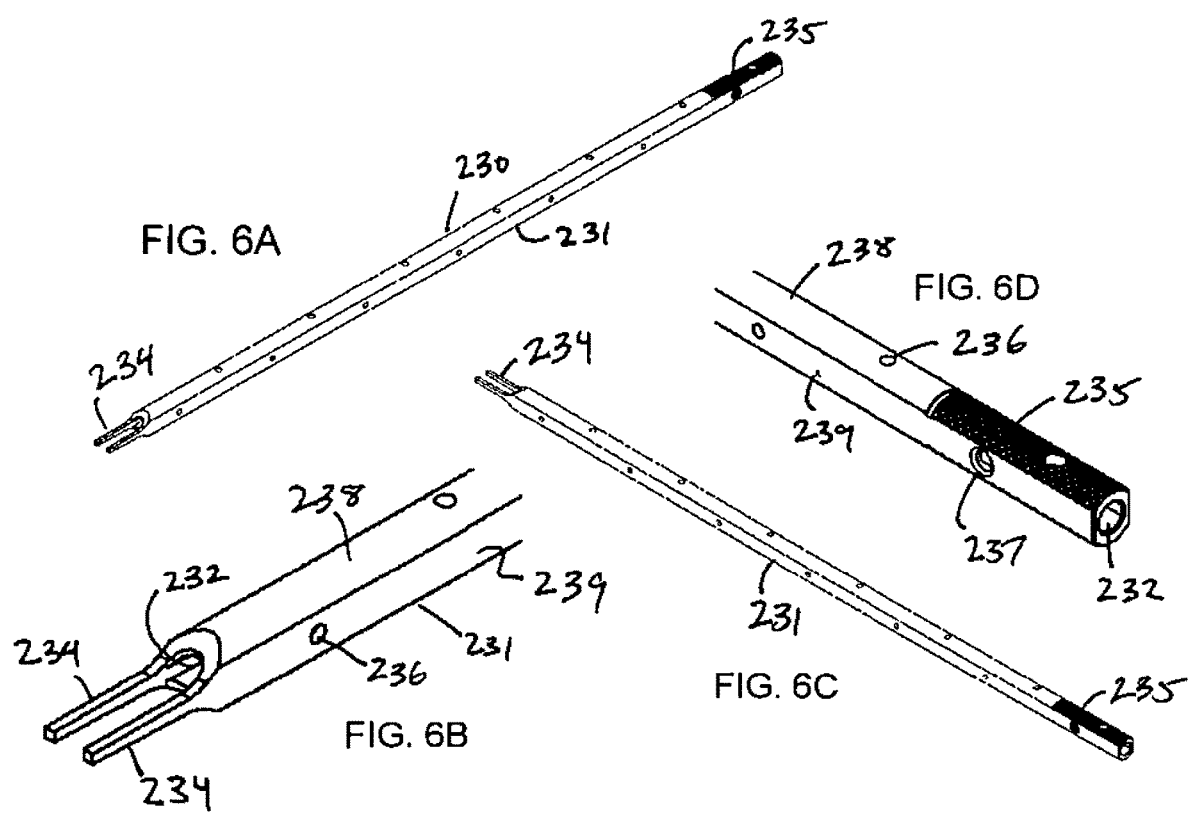

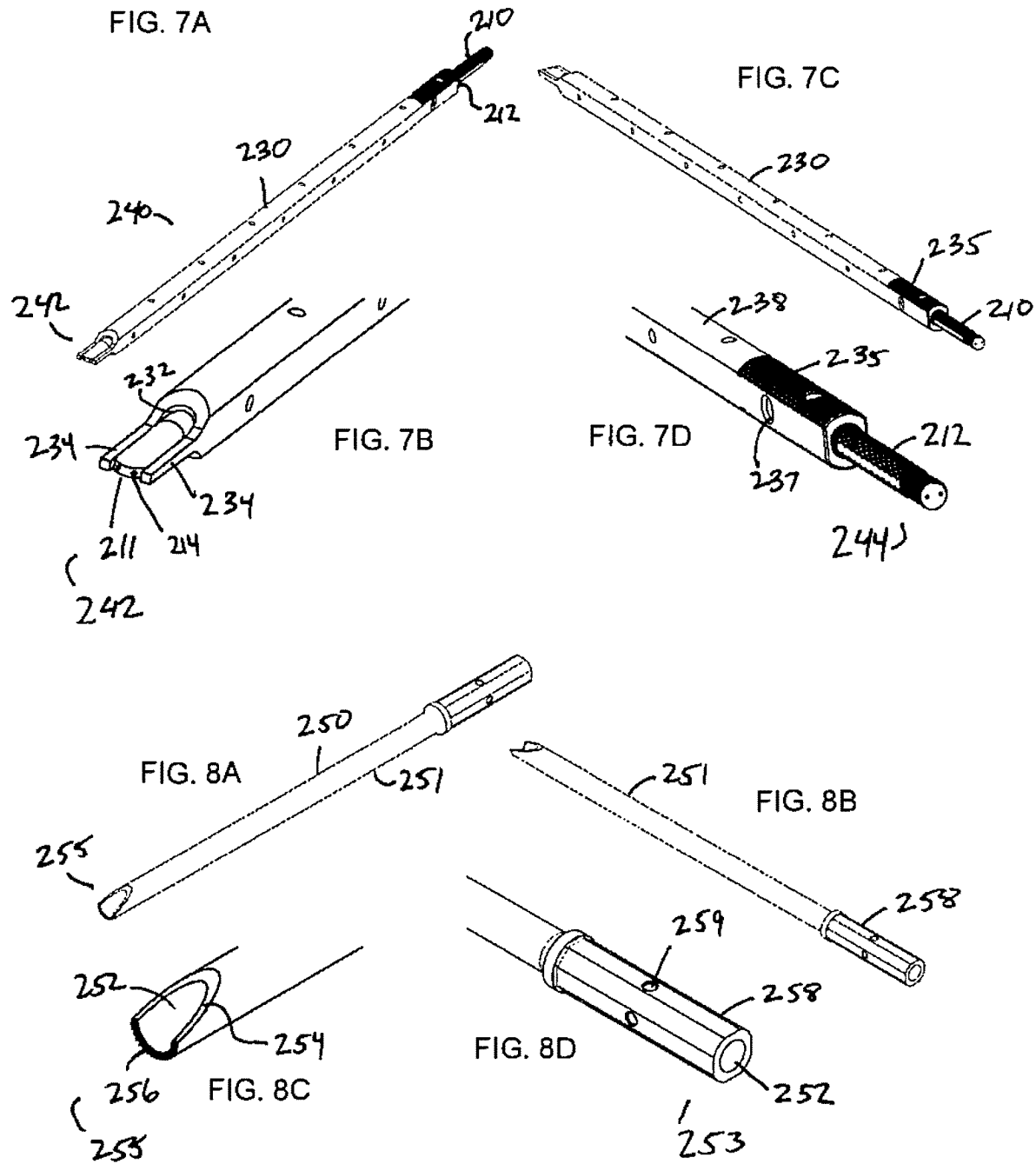

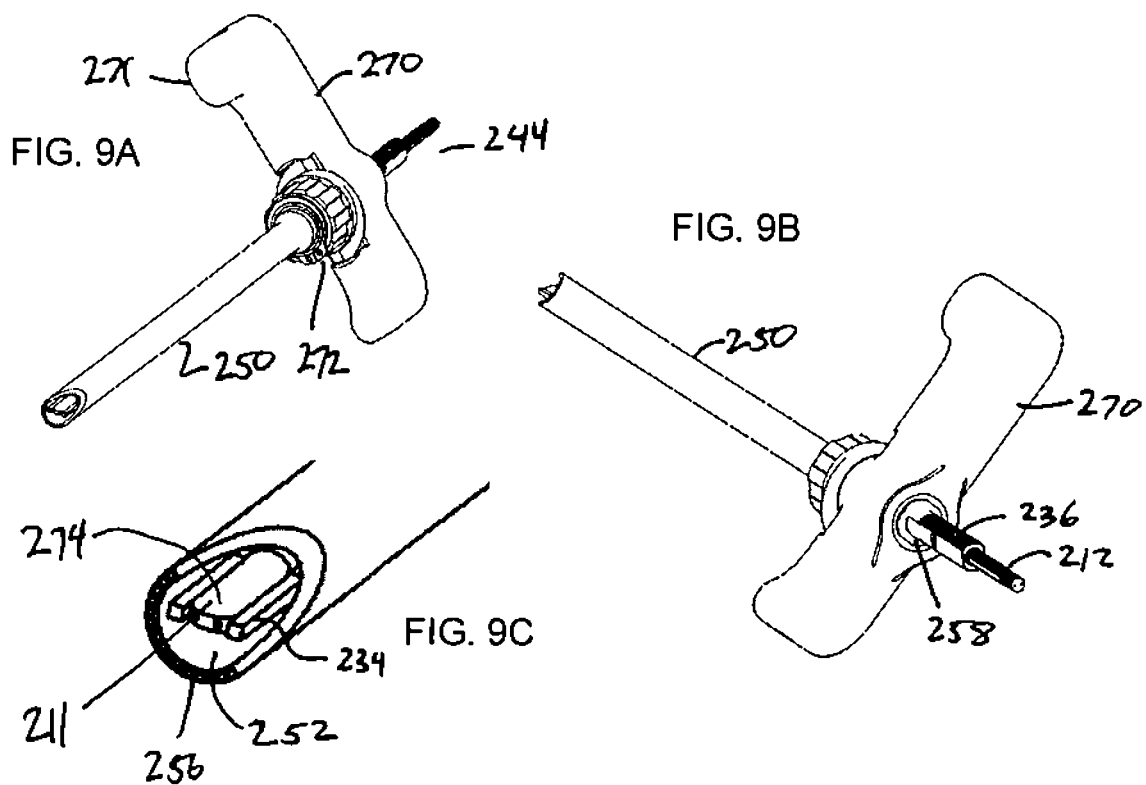
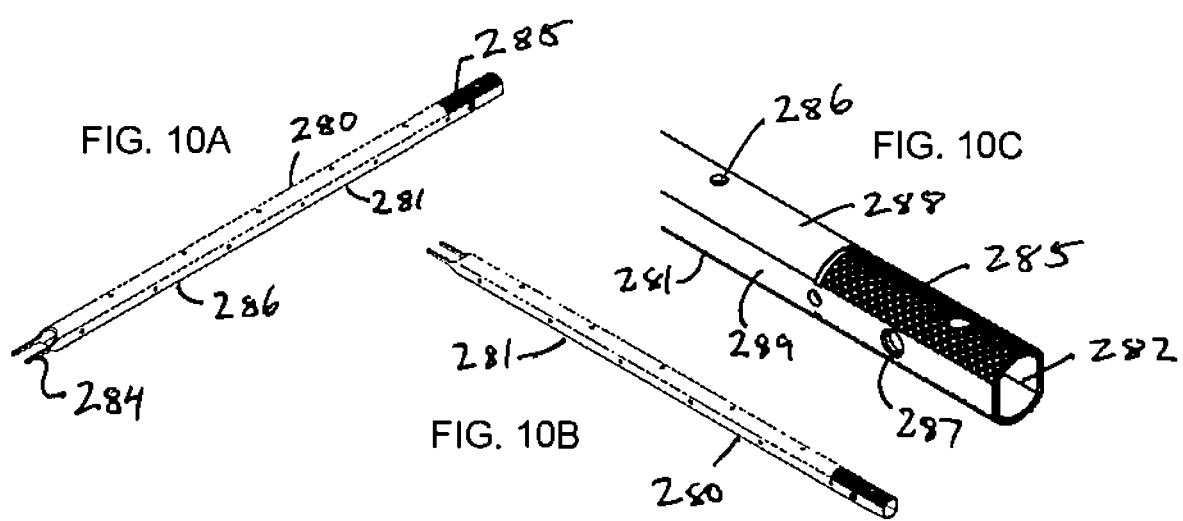

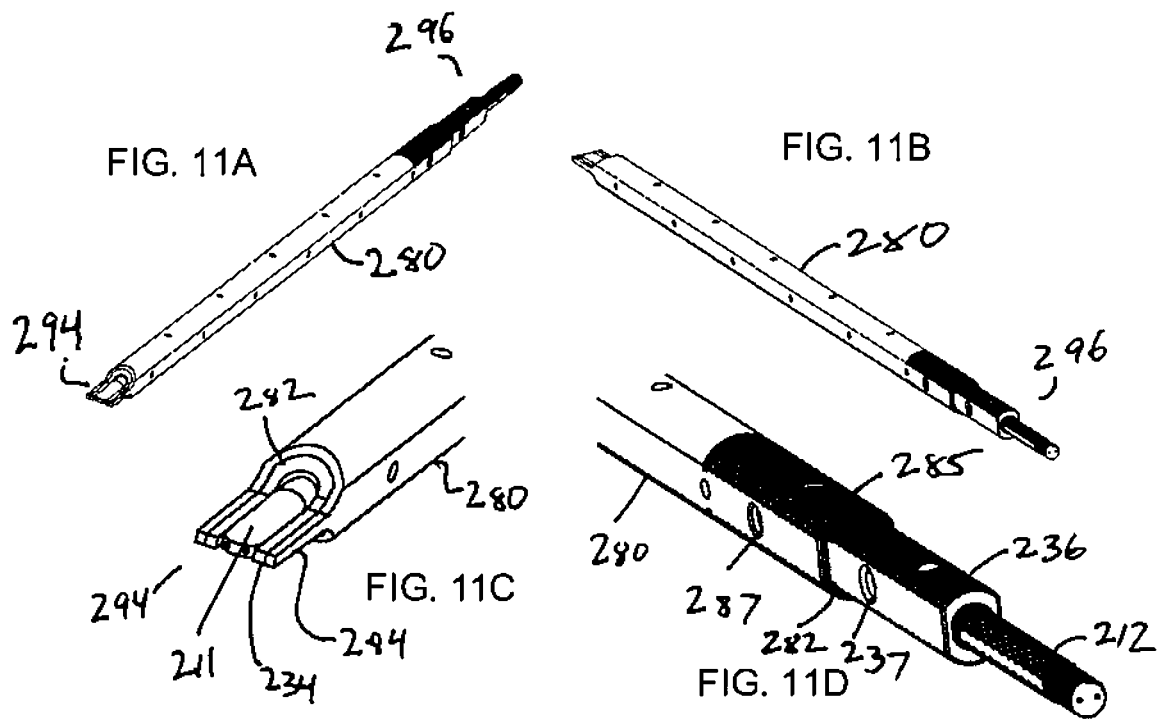
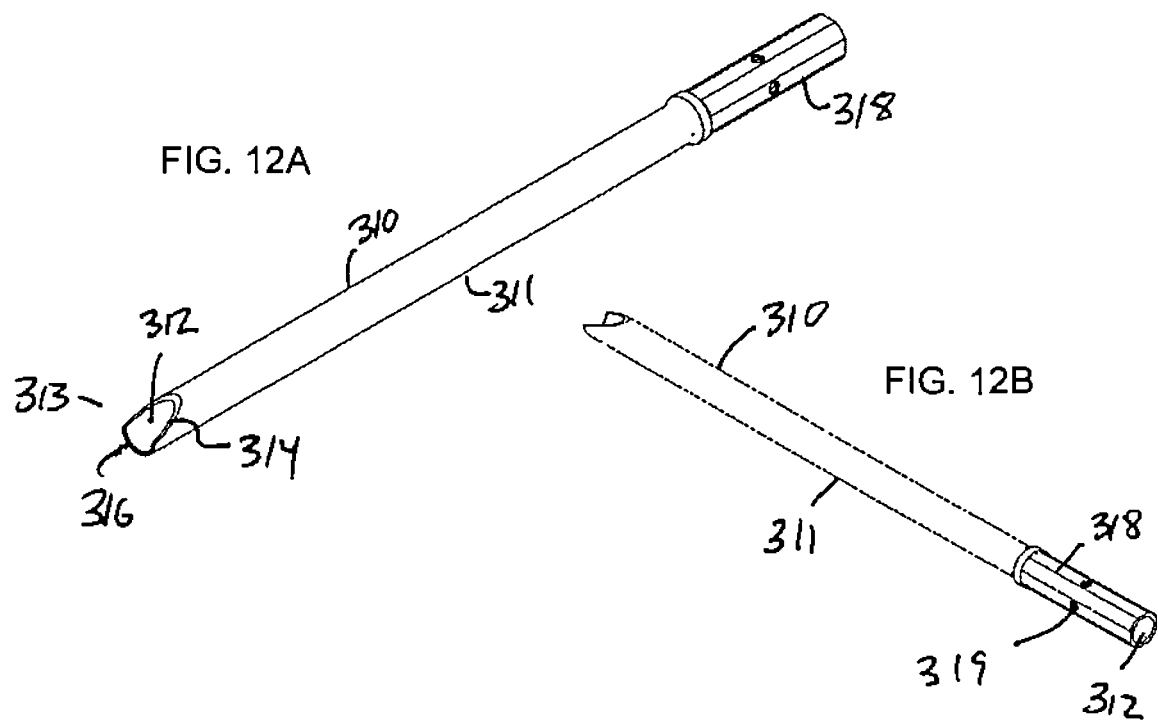

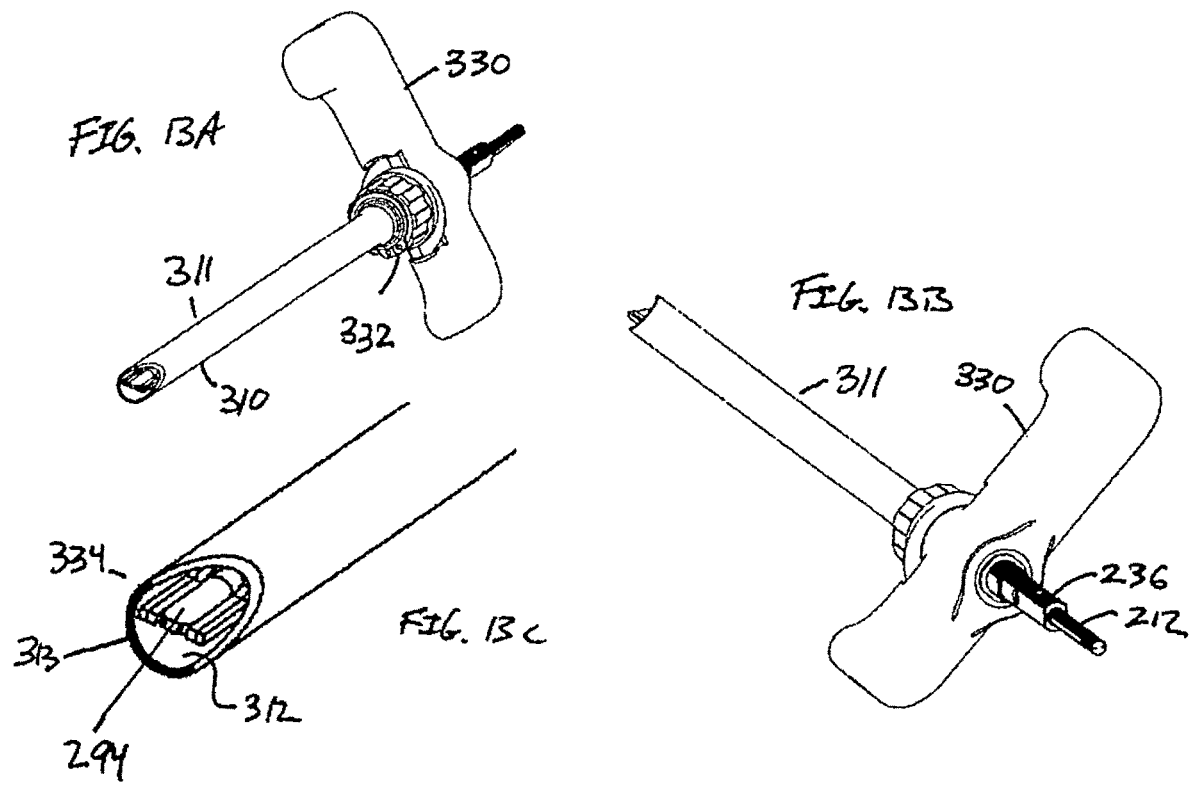
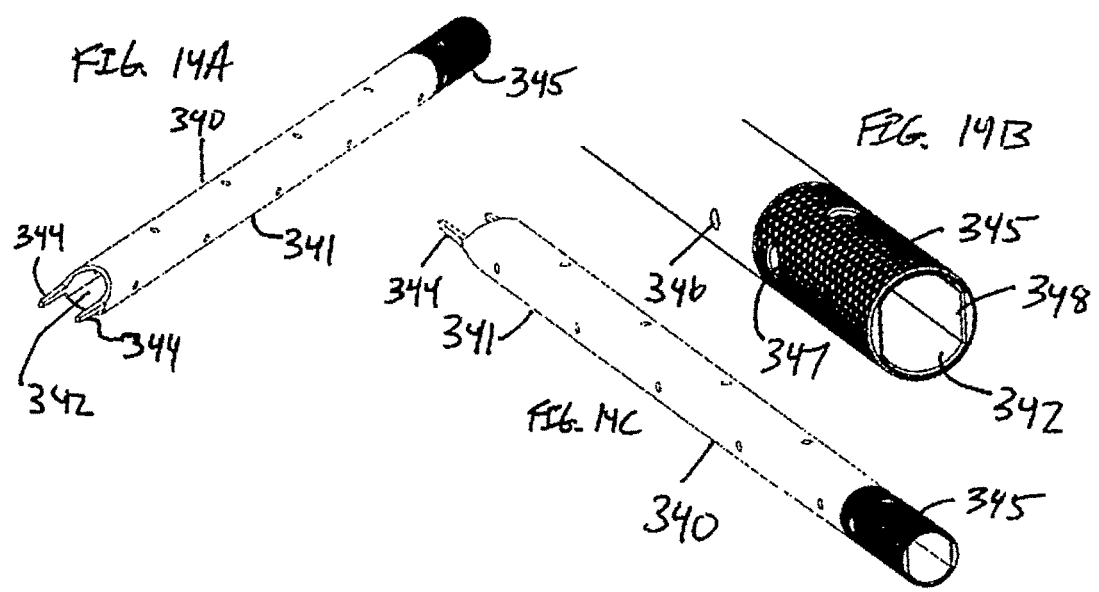

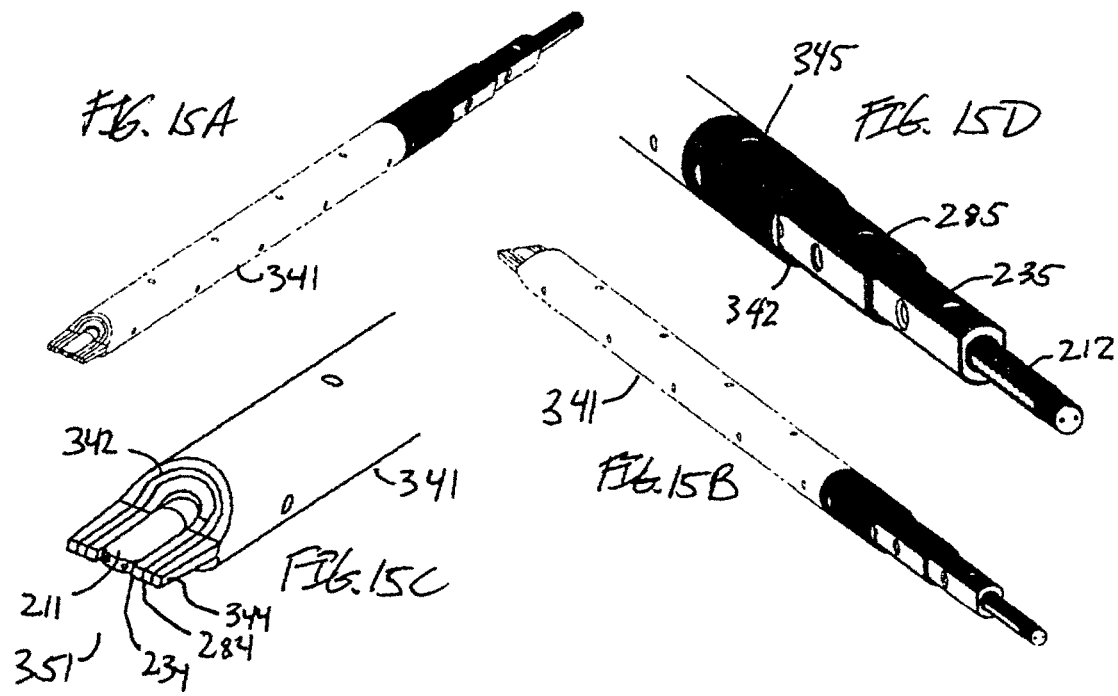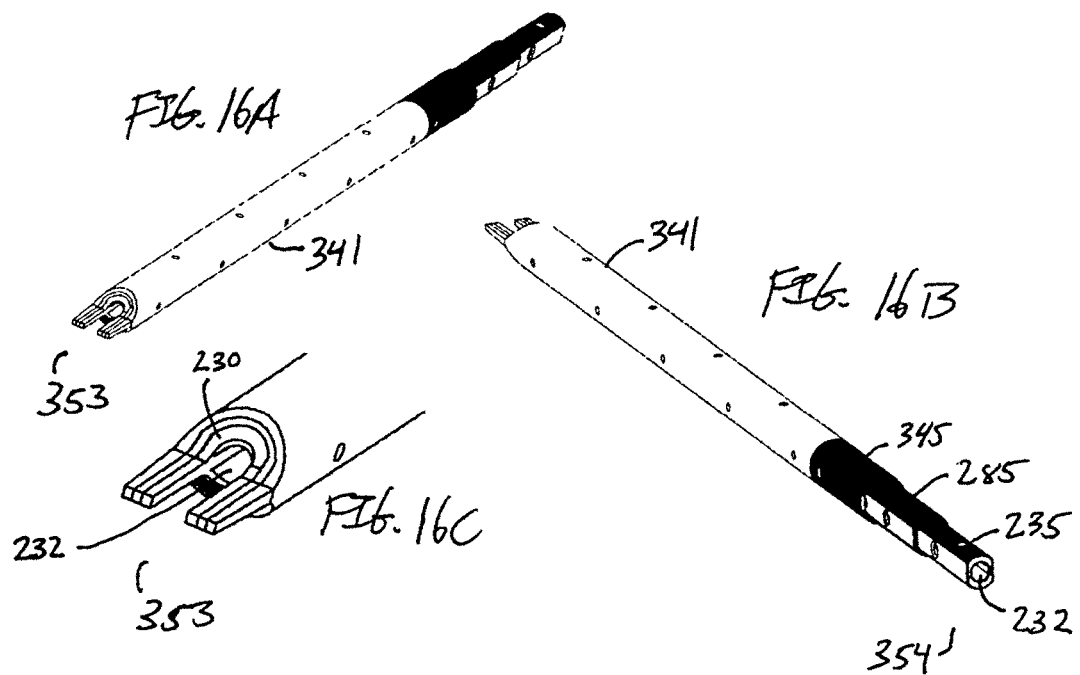

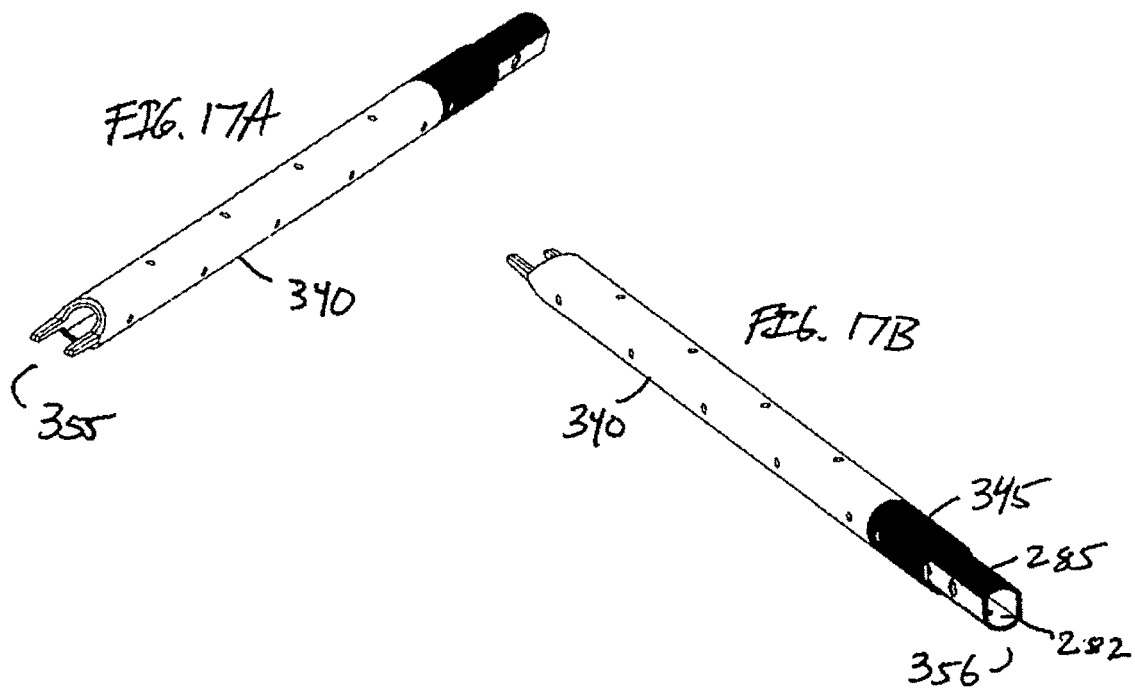
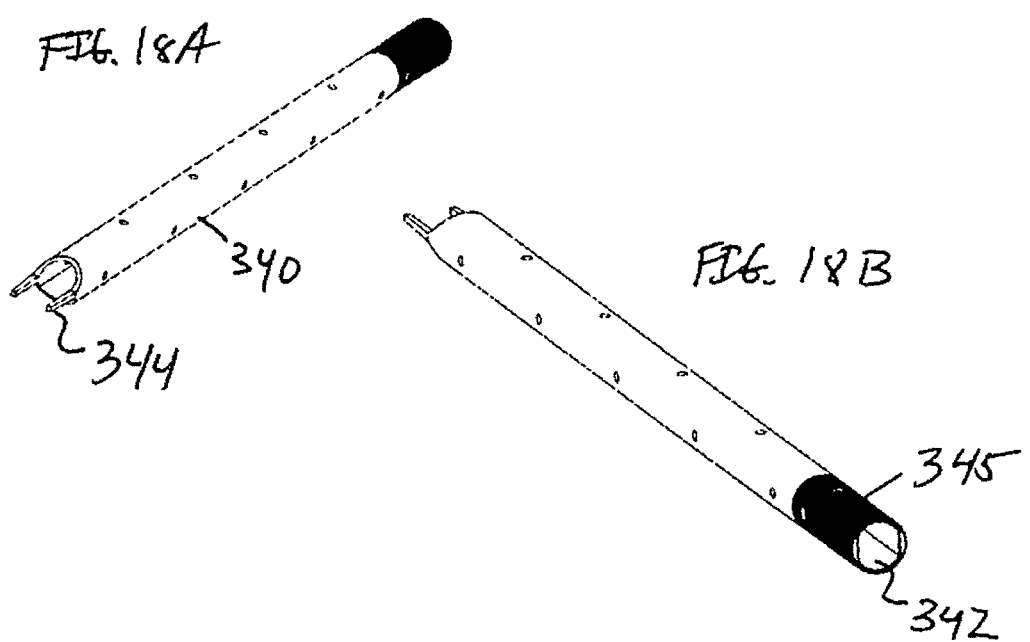

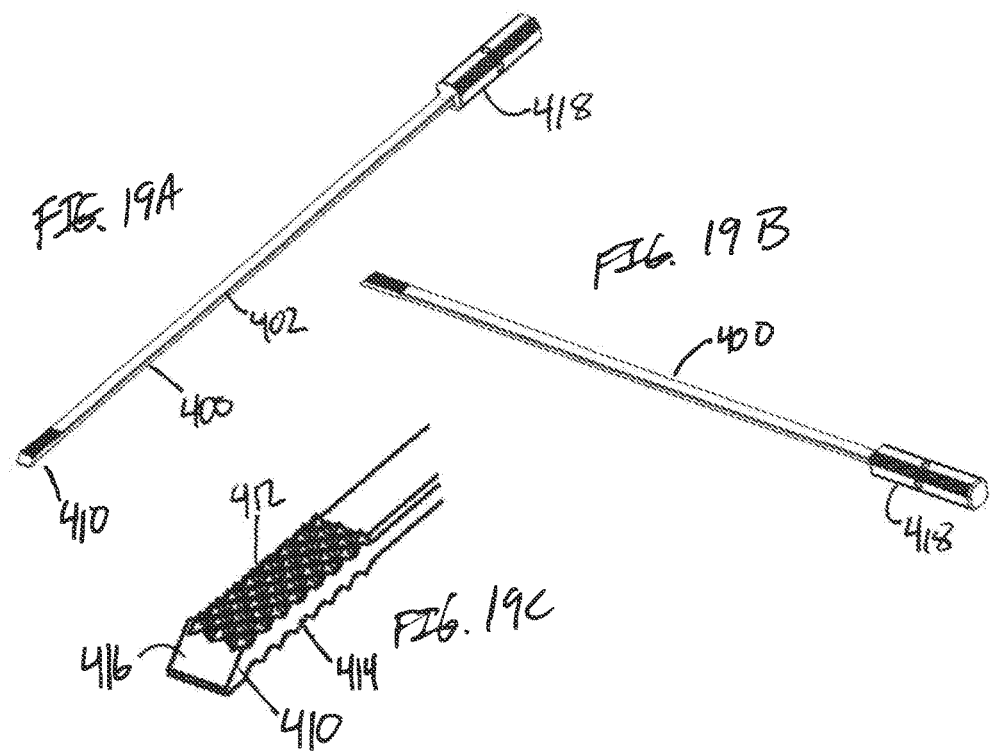
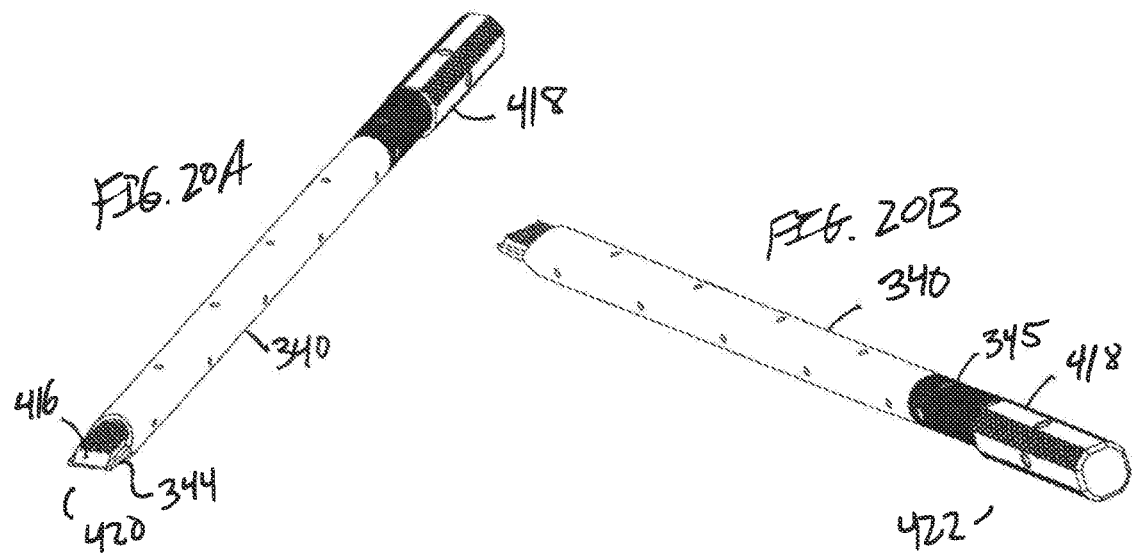

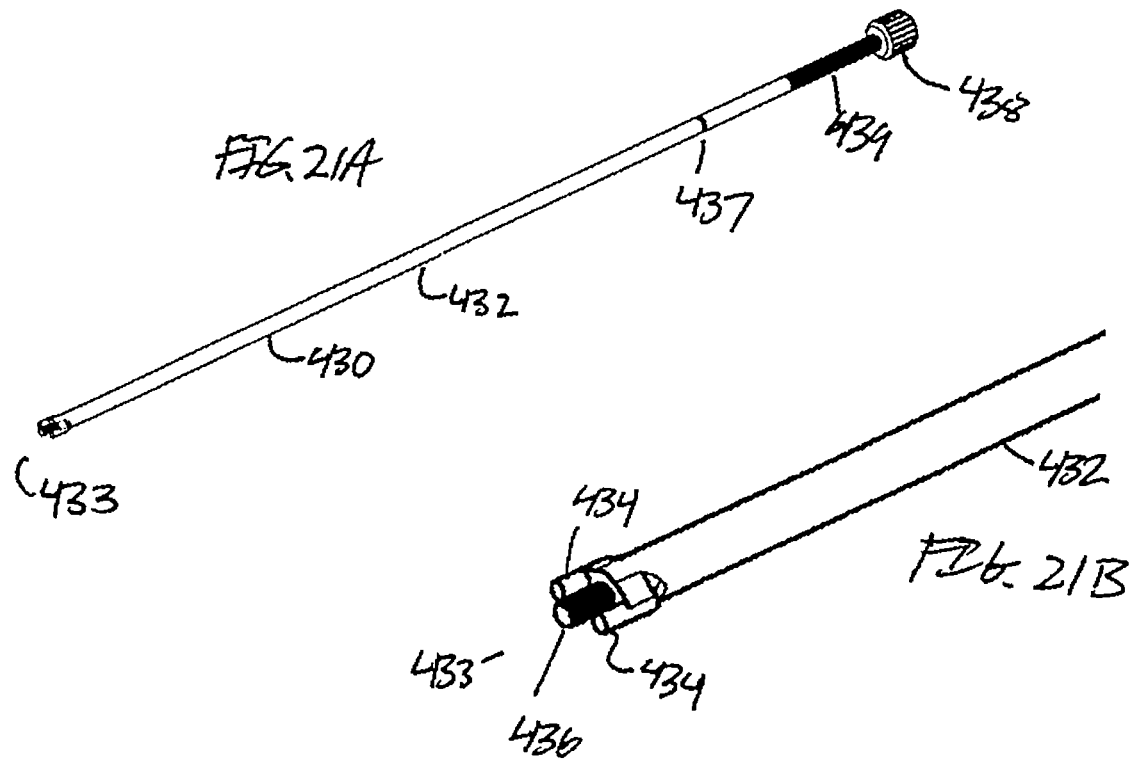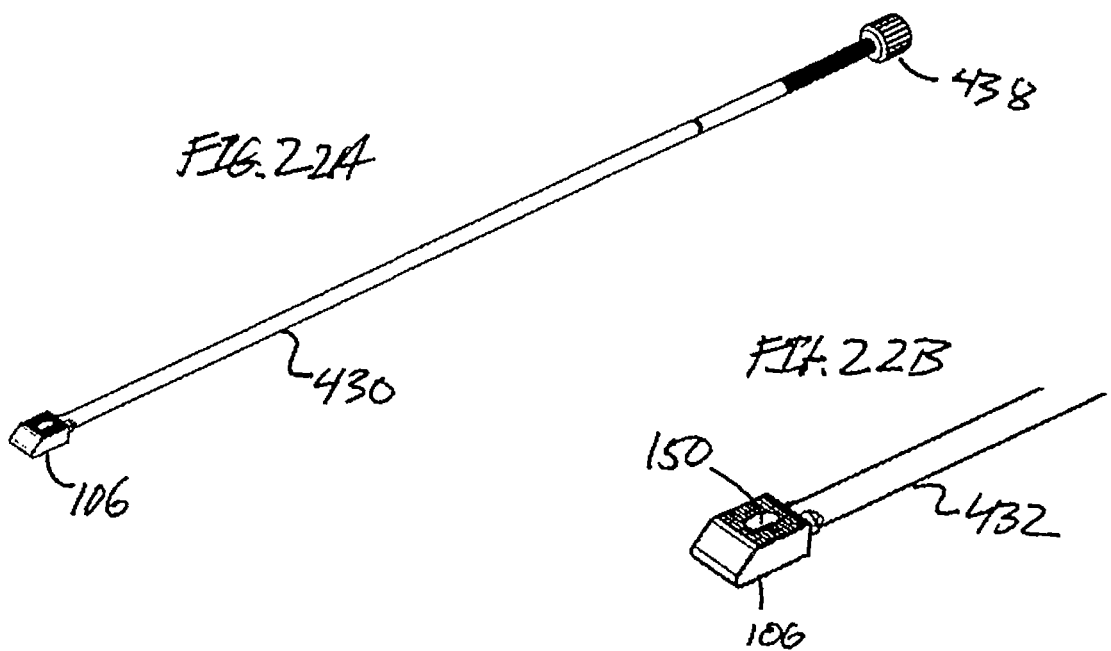

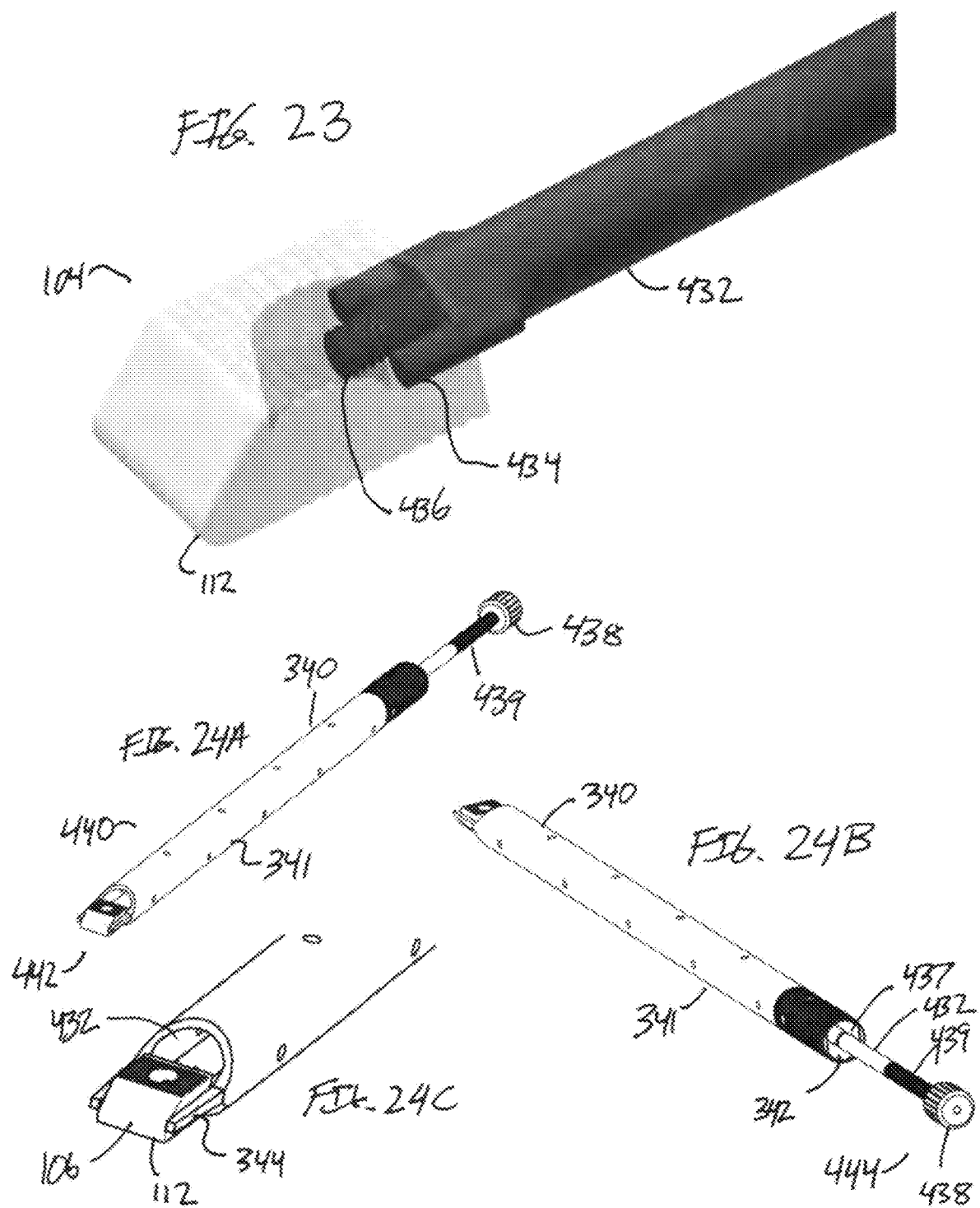

MINIMALLY INVASIVE POSTERIOR CERVICAL FACET ARTHRODESIS SHIM IMPLANT AND TOOLS THEREFOR

FIELD OF THE INVENTION

The invention pertains to surgical implants and tools for the distraction and fusion of cervical facet, foramen, and vertebrae.

BACKGROUND

Cervical spinal surgery since the late 1950s and early 1960s has steadily transitioned from primarily posterior based to primarily anterior based. Posterior based surgery has the following major advantages: minimal critical structures in the surgical field, familiar anatomy, and access to multiple levels. However, posterior based surgery has the following major disadvantages: dissection or approach related post-operative pain and large or limited arthrodesis option (for example, lateral mass screws and surface area available for fusion). Anterior based cervical surgery addresses some of the deficits, particularly pain and infection rates. Thus, the trend in the United States has been a shift towards more anterior cervical surgery and towards less posterior cervical surgery.

However, certain unique risks still remain with anterior surgery: injury to esophagus, injury to trachea, dysphagia/dysphonia, injury to recurrent laryngeal nerves, carotid artery injury, internal jugular vein injury, vagus nerve injury, adjacent level disease, non-unions, implant failure, implant prominence, dural injury, spinal cord injury to name a few. Thus, there has been a reemergence of posterior based surgery, particularly minimally invasive posterior surgery, to address the issues that may arise with anterior surgery.

Common indications for posterior minimally invasive surgery (MIS) include anterior cervical non-unions, patients at high risk for non-unions (for example, smokers), and/or isolated foraminal stenosis which may lead to radiculopathy. In theory, given that the facet surface area of the posterior spine is equal to or larger than the surface area of the disc space anteriorly in between the uncus, one could minimize the rate of cervical non-unions or even treat anterior non-unions via a posterior MIS. In theory, if stenosis is present at the foraminal level, indirect decompression via a posterior MIS would elevate the facet joint and increase the foraminal height as has been shown in the literature. In theory, given the minimal disruption of soft tissue with posterior MIS, the infection rates and post-operative pain issues would match or surpass that of anterior based surgery.

Two general technologies are currently in use for minimally invasive cervical facet arthrodesis. The first are manufactured allografts, made from human bone that is compacted and machined. See for example "FacetLift" implants from Medtronic. These implants have clear disadvantages. The implants are brittle and can fracture during insertion. In addition, these implants are radiographically lucent, which can make intra-operative assessments challenging and post-operative fusion rates difficult to observe. And, these implants have small pore sizes (or no pores at all) from the machining process and can result in limited or no bone in-growth and bone fusion.

An alternative cervical facet implant are metal (usually titanium) implants, for example the "CAVUX®" (referred to as "DTRAX®" in some literature), "HONOUR® ORB," "Valeo® II C", "UNIFLEX® Cervical cage" and others. See, for example, WO 2015/047818 and WO 2009/148619. These implants do not provide for efficient bone in-growth. Rather, they typically have bone on-growth or through-growth through a limited graft window, which is less efficient at bone fusion. In addition, the shape of prior art implants is not conducive to safe implantation. In some instances, these implants require harsh insertion techniques, such as malleting that reduce the control of the implantation procedure. The cervical facet joints frequently have minor imperfections and bone spurs, and prior art devices can unnecessarily damage these features during implantation.

SUMMARY OF THE INVENTION

The inventive implants provide a novel combination of features that address the shortcomings in the prior art discussed above. In various embodiments, the inventive implants include a titanium or tantalum alloy body that has a similar modulus of elasticity as natural bone and provides good radiologic contrast. In an embodiment, the inventive implants include a rounded nose that limits tissue damage during insertion. In an embodiment, the inventive implants include serrated surfaces on the superior and inferior faces. In an embodiment, the body of the inventive implants may be porous, roughened, and coated with an osteoconductive material such as hydroxyapatite (HA) and/or tricalcium phosphate (TCP). In an embodiment, the body of the inventive implant includes a graft window spanning the entire thickness of the implant.

In an embodiment, implants and methods are provided for treating stenosis with or without radiculopathy comprising surgical distraction of the relevant cervical vertebrae and insertion of the implant of claim 1. In an embodiment, this invention provides a shim implant for the fusion of a cervical facet joint, comprising a generally rounded or box-shaped body having a distal face, a proximal face, superior and inferior surfaces in a generally parallel orientation, and two side faces in a generally parallel orientation, wherein a transverse axis can be defined as a line perpendicular to the side faces. The distal face may have a rounded profile defined by an arc having a radius on a transverse axis. The proximal face may have one or more insertion device engagement features. The superior and inferior surfaces each comprise serrations with a plurality of grooves on a transverse axis generally spanning the entire length of a transverse axis. The implant may be fabricated from titanium metal or alloy or tantalum metal or alloy, and may have a roughened surface, and is coated with hydroxyapatite or tri-calcium phosphate or both and is porous to allow for bone in-growth.

In an embodiment, the implant may have a graft window comprising a perforation spanning the distance between the superior and inferior surfaces. In an embodiment, the implant may have a rounded profile of the distal face is biased towards the inferior surface. In an embodiment, the insertion device engagement features comprise one or more holes in the proximal face. The insertion device engagement features may comprise three holes aligned on a transverse axis on the proximal face. At least one hole may have female screw threads for engaging a male threaded tool. The threaded hole may be a central hole in a group of three holes.

In an embodiment, each surface of the implant may be roughened with a macro surface roughener or nano-coating. In an embodiment, the hydroxyapatite or tri-calcium phosphate coating has a thickness of approximately 35 μm. The porous material may have pore sizes ranging in 200 to 900 μm.

In an embodiment, a set of tools is provided for implanting the implant described above. The tools include a chisel and one or more tongs and rasps. An entry chisel is provided with a distal end with smooth inferior and superior surfaces, and a uniform cross-sectional profile, wherein the chisel has a shaft with rounded superior and inferior surfaces and flattened sides, and wherein the chisel shaft has two cannulation channels running the entire length thereof for accepting a guidewire. In an embodiment, a first tong has two prongs at a distal end that are smooth or roughened, and a channel in the shaft along the entire length of the tong, and the interior cross-section of the channel matches the uniform cross-sectional profile of the chisel, such that the chisel can be inserted in the channel in the first tong from a proximal end of the first tong to a nested position. The rounded superior and inferior surfaces and flattened sides of the chisel maintain rotational stability that prevents the chisel from rotating when in place. When nested, the distal tip of the chisel may be aligned with the prongs. The chisel nested in the first tong may be inserted into a channel in a proximal end of a first decorticator, wherein the first decorticator has a jagged distal end with teeth and the proximal end has a handle for manual manipulation of the decorticator, and wherein the chisel and first tong are aligned with the distal edge of the first decorticator, and wherein a facet joint between two vertebrae is decorticated from a posterior approach. The first decorticator may then be withdrawn leaving the chisel nested in the first tong embedded in the facet joint and the chisel may then be withdrawn. Next, a rasp may then be inserted into the channel in the first tong. A rasp of various dimensions (width and height) may be used to remove tissue within the facet joint to facilitate a fusion and to gauge the width and height of the final implant. The rasp is then withdrawn from the channel in the first tong. Next, an inserter having an implant as described above affixed to it is inserted into the channel in the first tong. In an embodiment, the inserter may have a shaft, an axle within the shaft, a handle that turns the axle, and a male-threaded connection at the distal end of the axle that is screwed into the female-threaded engagement feature on the implant, and at least one prong aligned with another engagement feature on the proximal face of the implant. The inserter is inserted into the channel in the first tong, and the implant is placed and secured in the facet joint. The handle is rotated to unscrew the implant and disconnect the implant from the inserter, and the first tong is withdrawn, leaving the implant securely in position.

In an embodiment, a second tong may be provided having two prongs at a distal end that are smooth or roughened and a channel in the shaft along the entire length of the second tong, wherein the interior cross-section of the channel matches the uniform cross-sectional profile of the first tong. The chisel nested in the first tong is inserted into the proximal end of the channel on the second tong into a nested position wherein the chisel tip, prongs of the first tong, and prongs of the second tong may be aligned. The chisel nested in the first tong and nested in the second tong may then be inserted into the facet joint. In an embodiment, the chisel and first tong are withdrawn, and a rasp may be inserted into the channel in the second tong. Rasps of various dimensions (width and height) may be manipulated by the surgeon to remove tissue within the facet joint to facilitate a fusion and to gauge the width and height of the final implant. The rasp may then be withdrawn from the channel in the first tong, and an inserter as described above having an implant as described above affixed to it, is inserted into the channel in the second tong, and the implant is placed and secured in the facet joint. The handle may be rotated to disconnect the implant from the inserter, and the second tong is withdrawn, leaving the implant securely in position.

In an embodiment, a second decorticator may be provided and the chisel nested in the first tong nested in the second tong are inserted therein to further decorticate the facet joint. In an embodiment, a third tong is provided that the chisel, the first tong and the second tong are inserted within to provide an appropriate space for the implant in a facet joint.

In an embodiment, the width of the space decorticated for the implant in the facet joint is controlled by the use of one or more tongs, and the height of the space decorticated for the implant is controlled by the height of the rasp.

DESCRIPTION OF THE DRAWINGS

FIG. 5A, FIG. 5B, and FIG. 5C depict an entry chisel according to an embodiment of this invention.

FIG. 6A, FIG. 6B, FIG. 6C and FIG. 6D depict a first facet tong according to an embodiment of this invention.

FIG. 7A, FIG. 7B, FIG. 7C and FIG. 7D depict the entry chisel nested within the first facet tong.

FIG. 8A, FIG. 8B, FIG. 8C and FIG. 8D depict a first decorticator tool according to an embodiment of this invention.

FIG. 9A, FIG. 9B and FIG. 9C depict the apparatus as shown in FIG. 7 nested inside the first decorticator. The decorticator includes a removable handle.

FIG. 10A, FIG. 10B, and FIG. 10C depict a second facet tong.

FIG. 11A, FIG. 11B, FIG. 11C and FIG. 11D depict the apparatus of FIG. 7 nested inside the second facet tong.

FIG. 12A and FIG. 12B depict a second decorticator according to an embodiment of this invention.

FIG. 13A, FIG. 13B, and FIG. 13C depict the apparatus of FIG. 11 nested inside the second decorticator.

FIG. 14A, FIG. 14B, and FIG. 14C depict a third facet tong according to an embodiment of this invention.

FIG. 15A, FIG. 15B, FIG. 15C and FIG. 15D depict the apparatus of FIG. 11 nested inside the third facet tong according to an embodiment of this invention.

FIG. 16A, FIG. 16B and FIG. 16C depict the apparatus of FIG. 15 with the entry chisel removed according to an embodiment of this invention.

FIG. 17A and FIG. 17B depict the apparatus of FIG. 16 with the first tong removed according to an embodiment of this invention.

FIG. 18A and FIG. 18B depict the apparatus of FIG. 17 with the second tong removed.

FIG. 19A, FIG. 19B and FIG. 19C depict a rasp tool according to an embodiment of this invention.

FIGS. 20A and 20B show the rasp apparatus inserted into the third tong according to an embodiment of this invention.

FIGS. 21A and 21B show an inserter tool according to an embodiment of this invention.

FIGS. 22A and 22B depict the inserter tool with an exemplary implant affixed to the distal end.

FIG. 23 is a cutaway view showing an implant according to an embodiment of this invention affixed to the distal end of the inserter tool.

FIG. 24A, FIG. 24B, and FIG. 24C depict a final set up with a rasp nested in the third tong according to an embodiment of this invention.

DETAILED DESCRIPTION

Figure 1A:
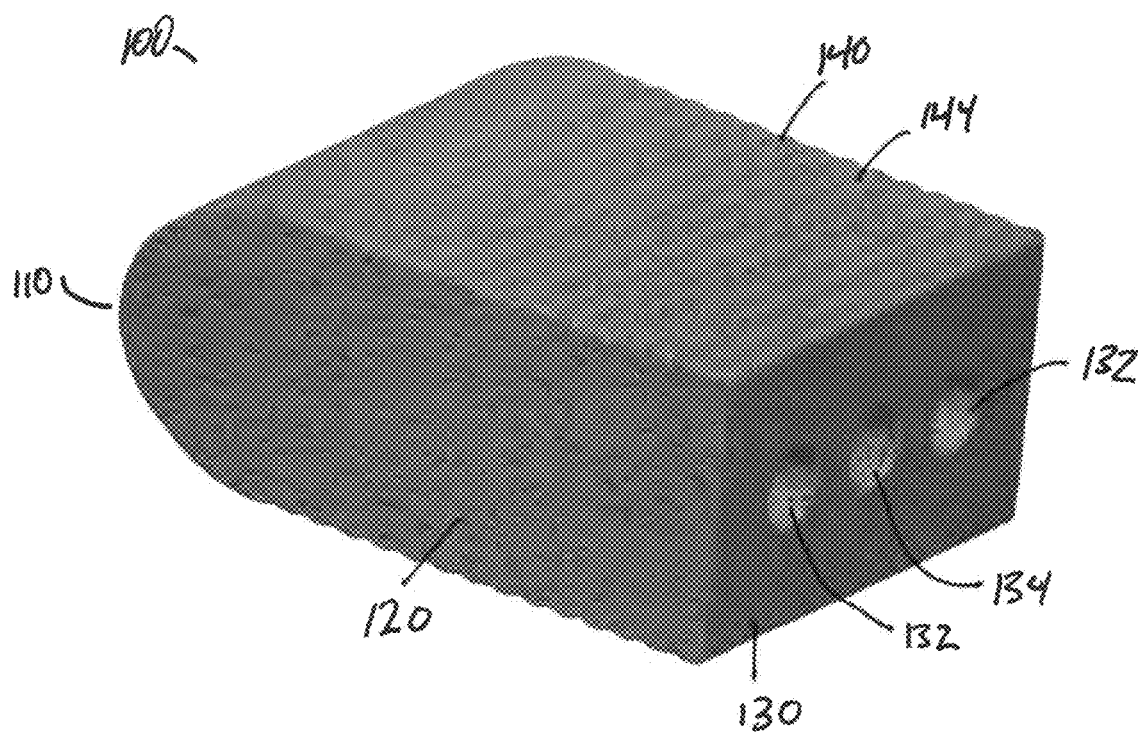
FIG. 1A is a perspective view of an embodiment of the inventive implant with a centered nose and without a graft window.
Figure 1B:
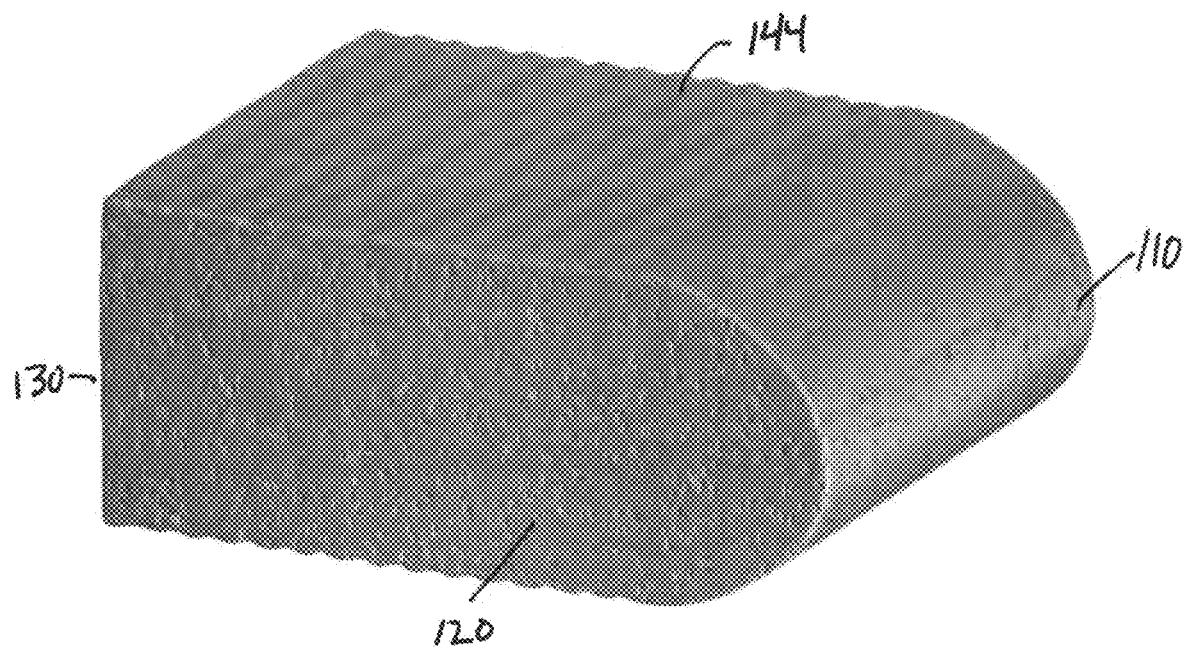
FIG. 1B is a perspective front view of the inventive implant of FIG. 1A.
Figure 1C:
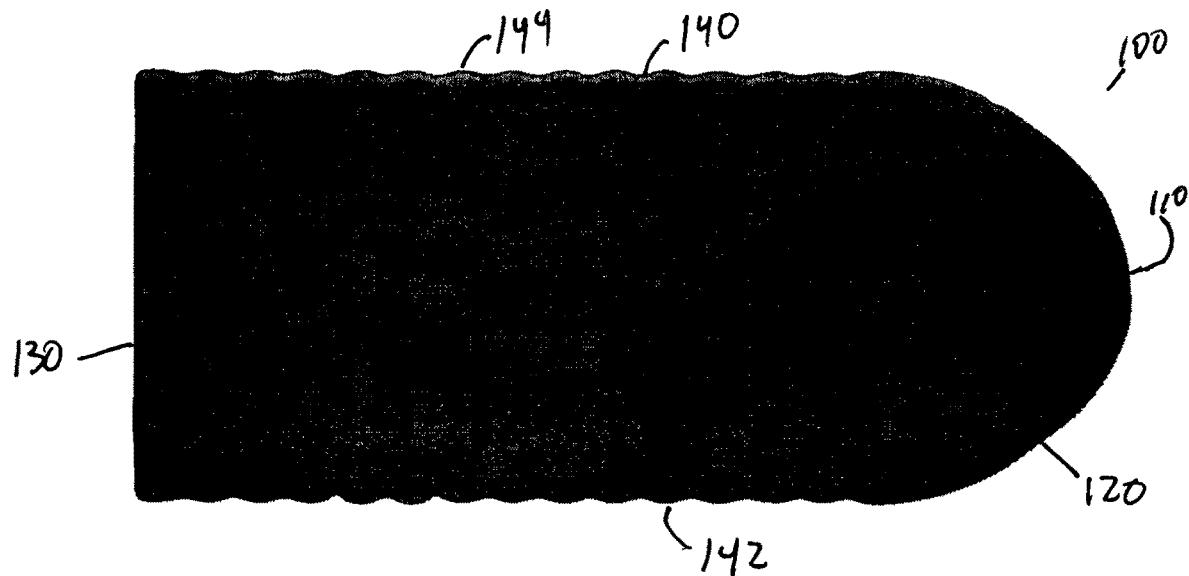
FIG. 1C is a side elevation view of the inventive implant of FIG. 1A.
Figure 1D:
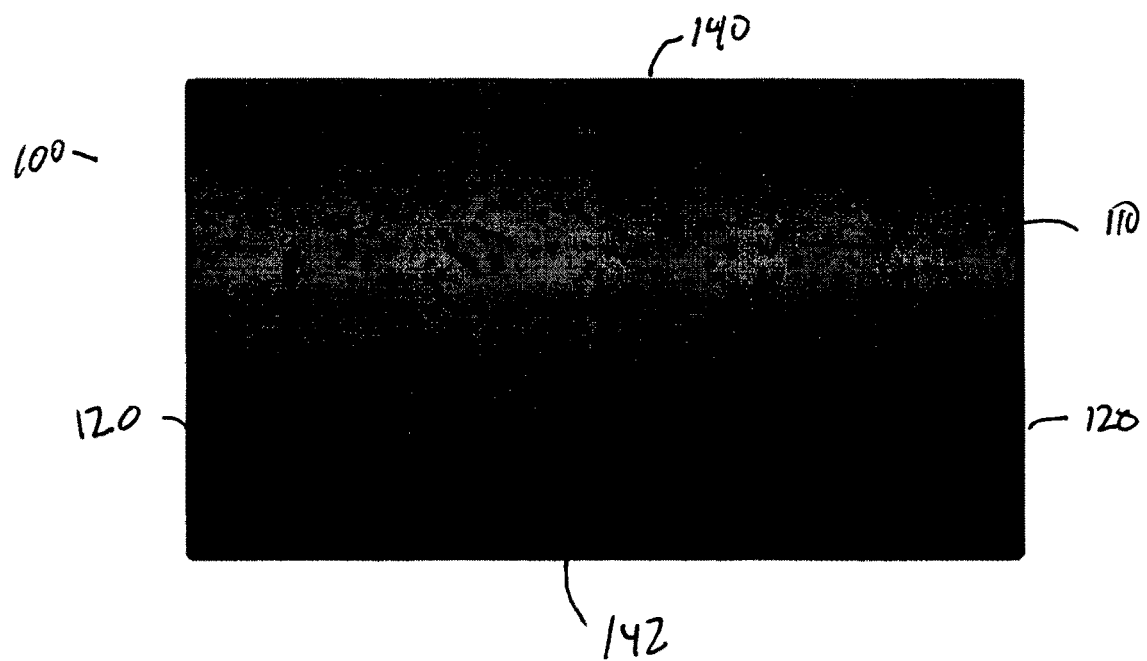
FIG. 1D is a front elevation view of the proximal end of the inventive implant of FIG. 1A.
Figure 1E:
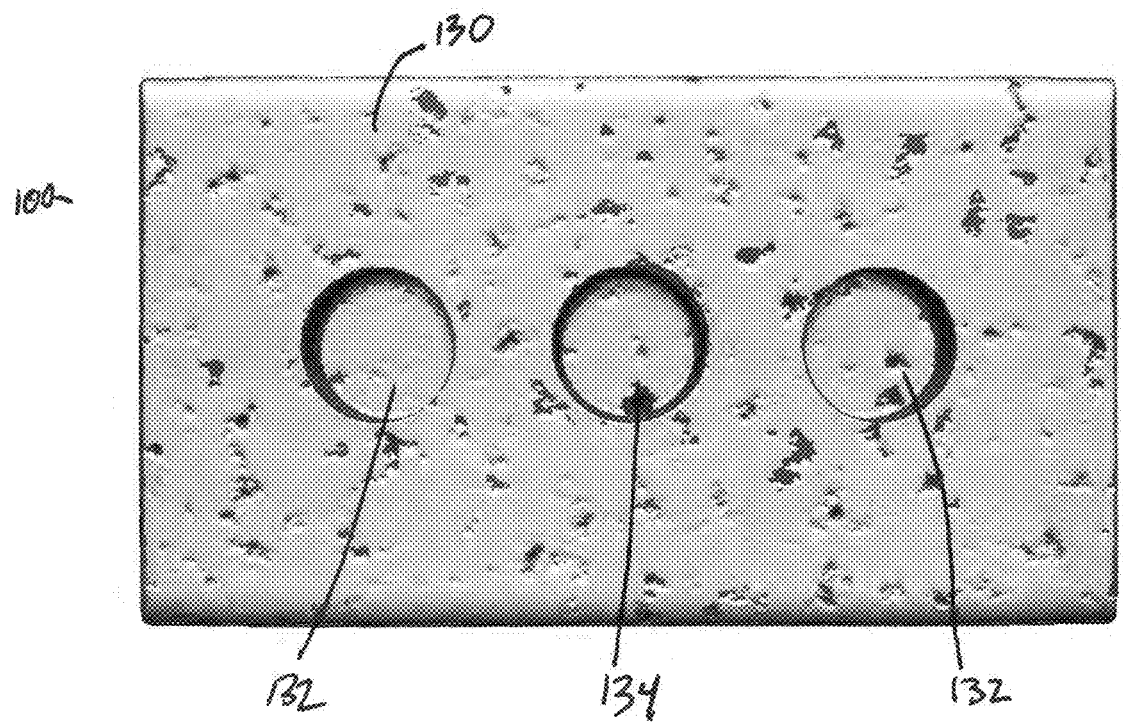
FIG. 1E is a back-elevation view of the inventive implant of FIG. 1A.

This invention provides an implant for the fusion of cervical spinal vertebrae, tools to insert the implant, and surgical procedures.

Implants

In an embodiment, the implant is a shim 100 with a box-shaped body as shown in FIGS. 1A-1E. For orientation, the shim has a blunt distal end that would sit anteriorly within the facet joint, also referred to herein as a nose, for insertion in between the cervical facet joints to minimize damage during insertion and reduce the tolerance necessary to insert the implant without unnecessary damage at the implant insertion site. The terminology "distal" and "proximal" are in relation to the surgeon implanting the inventive shim. Thus, the proximal face is closest to the surgeon during implantation, and the distal face is the leading edge inserted into the body of the patient at the implant site. The distal end of the implant, then, would sit more anteriorly within the facet joint, and the proximal end of the implant would sit more posteriorly within the facet joint.

In an embodiment, the inventive shim 100 has a proximal side with one or more insertion device engagement features 132 and 134. In an embodiment, the insertion device engagement features are one or more threaded (134) and non-threaded (130) holes or indents adapted to receive appropriate tools used to aid in the implantation of the inventive device. In the embodiment illustrated in the figures, there are three holes in the proximal face of the implant, and the center hole 134 is threaded. In an embodiment, the holes may be drilled into the implant after the body is formed or may be created as the implant is created using additive manufacturing techniques.

The inventive implants also have a superior face 140 and an inferior face 142. In an embodiment, the superior and inferior faces both have a series of parallel grooves or serrations 144 running in a transverse direction.

Figure 2A:
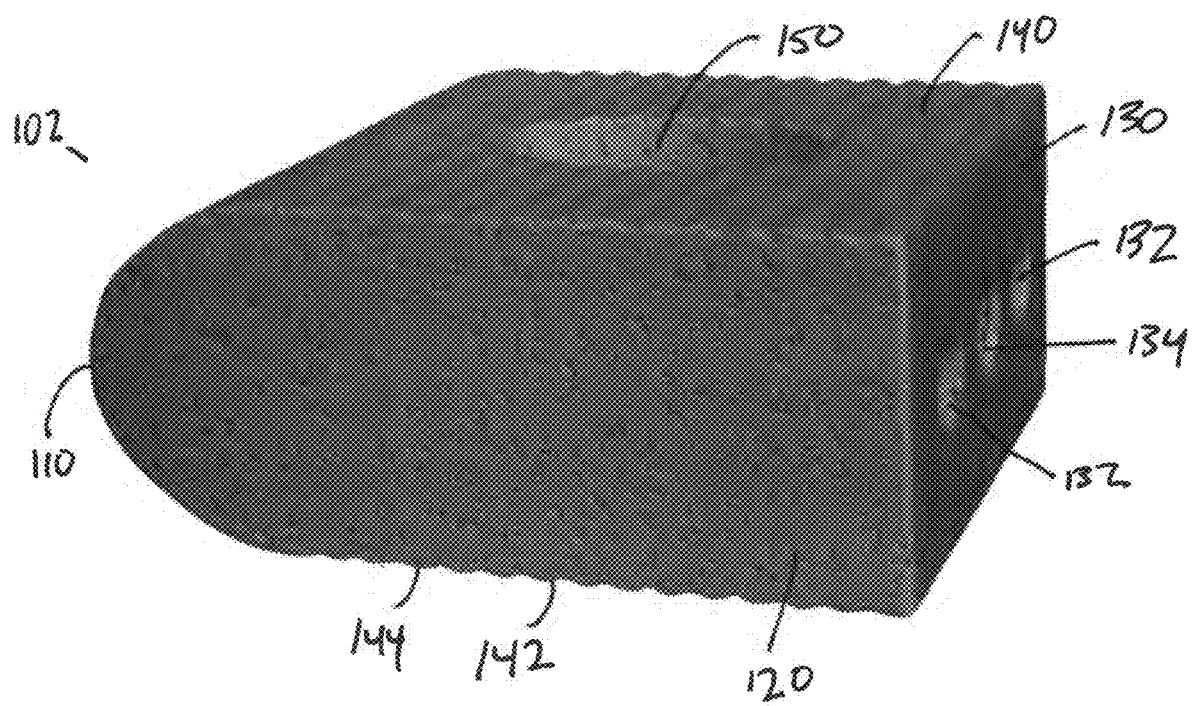
FIG. 2A is a perspective view from the rear and above of an embodiment of the inventive implant with a centered nose and with a graft window.
Figure 2B:
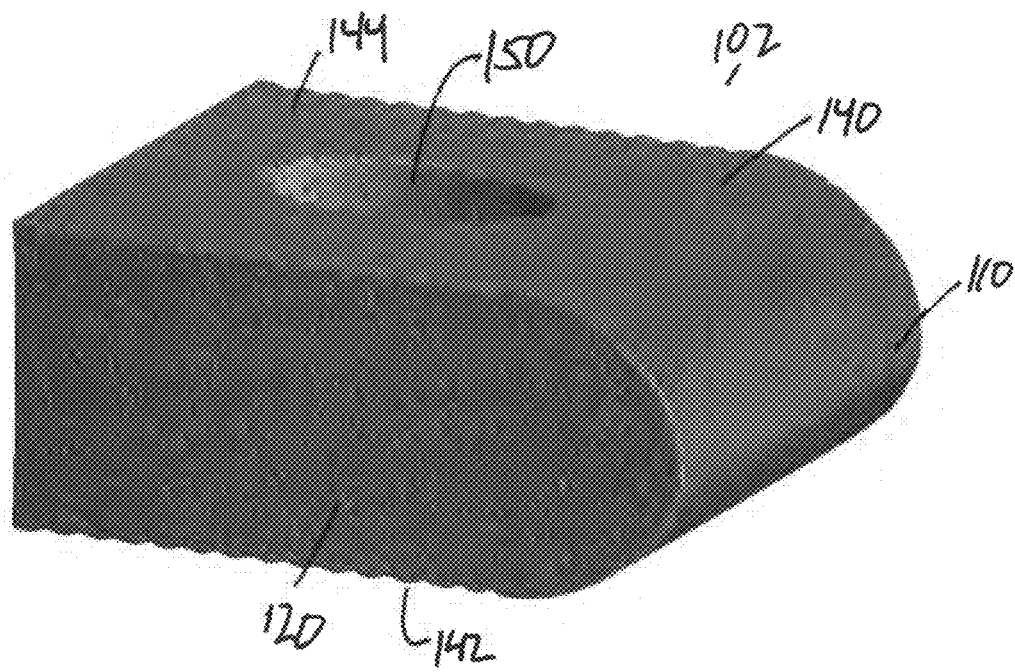
FIG. 2B is a perspective front view of the inventive implant of FIG. 2A.
Figure 2C:
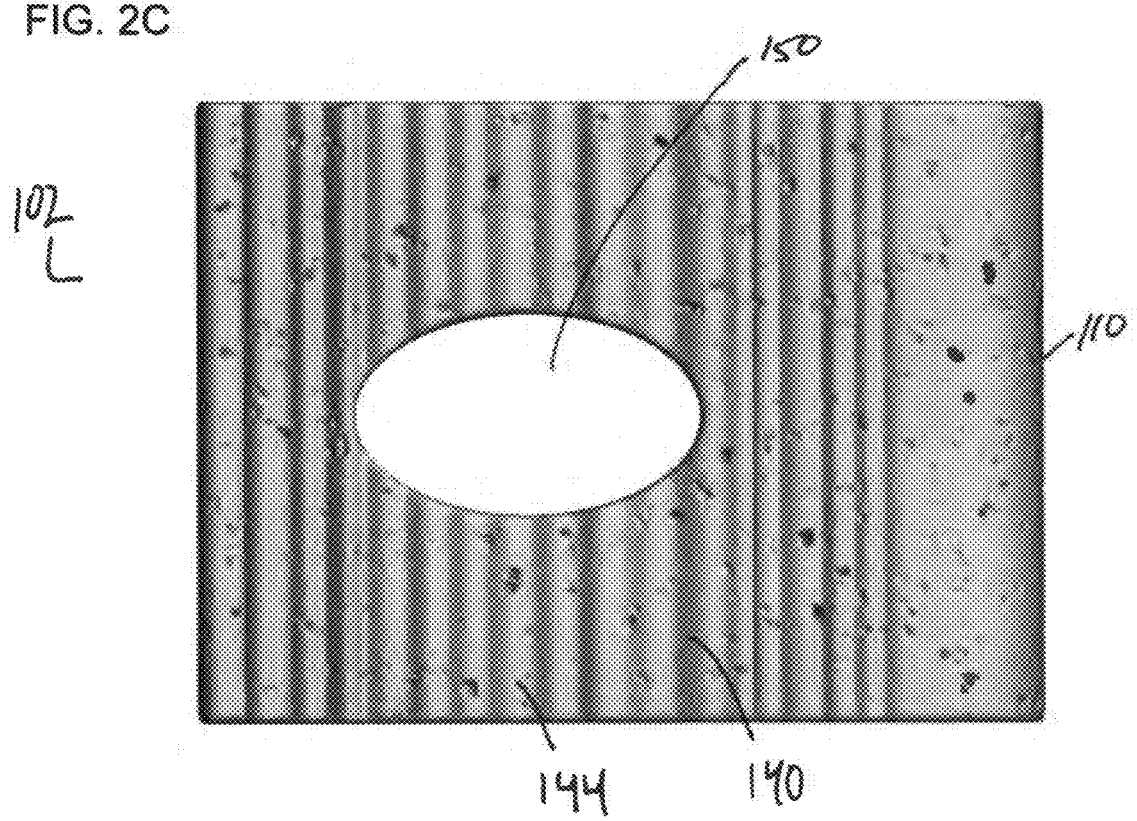
FIG. 2C is a top view of the inventive implant of FIG. 2A.

FIGS. 2, 3, and 4 all illustrate variations on the embodiment of FIG. 1. In FIGS. 2A and 2B, implant 102 is illustrated. This is similar to implant 100 but also features a graft window 150, that in an embodiment, is an aperture through the entire thickness of the implant 102 from the inferior surface to the superior surface.

Figure 3A:
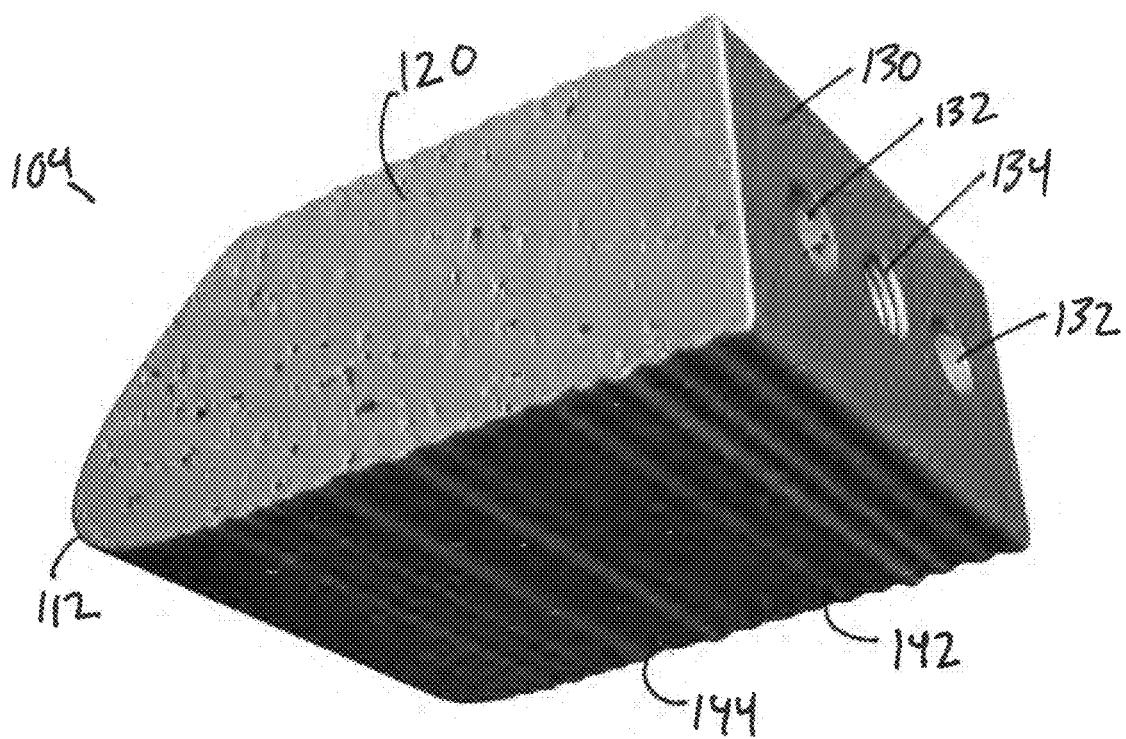
FIG. 3A is a perspective view from the rear and below of an embodiment of the inventive implant having a nose which is off center and no graft window.
Figure 3B:
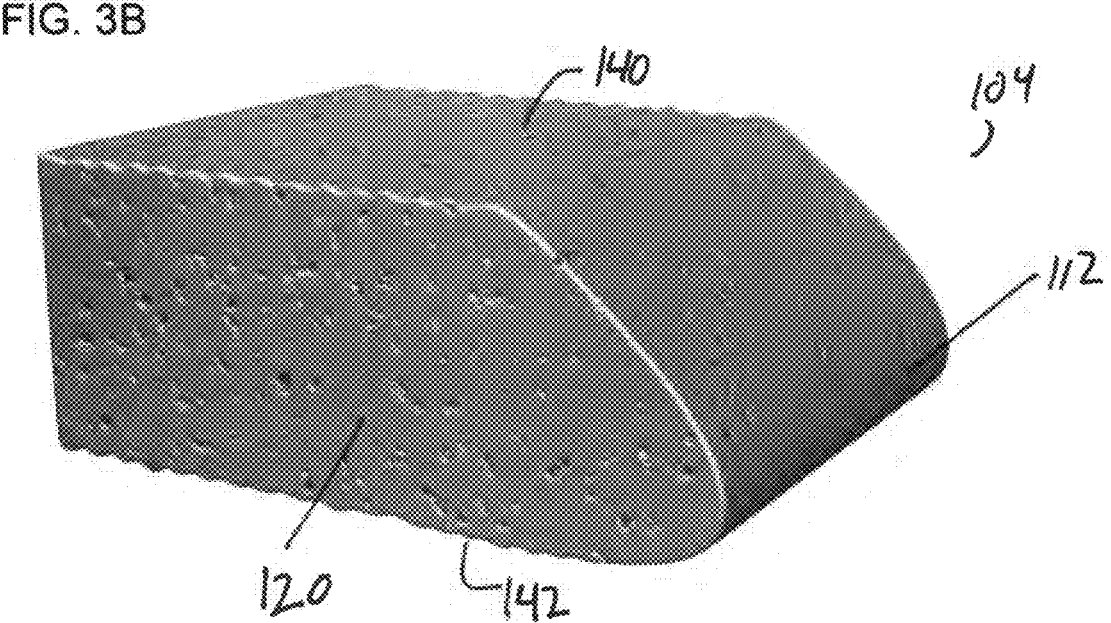
FIG. 3B is a front perspective view of the implant of FIG. 3A.
Figure 4A:
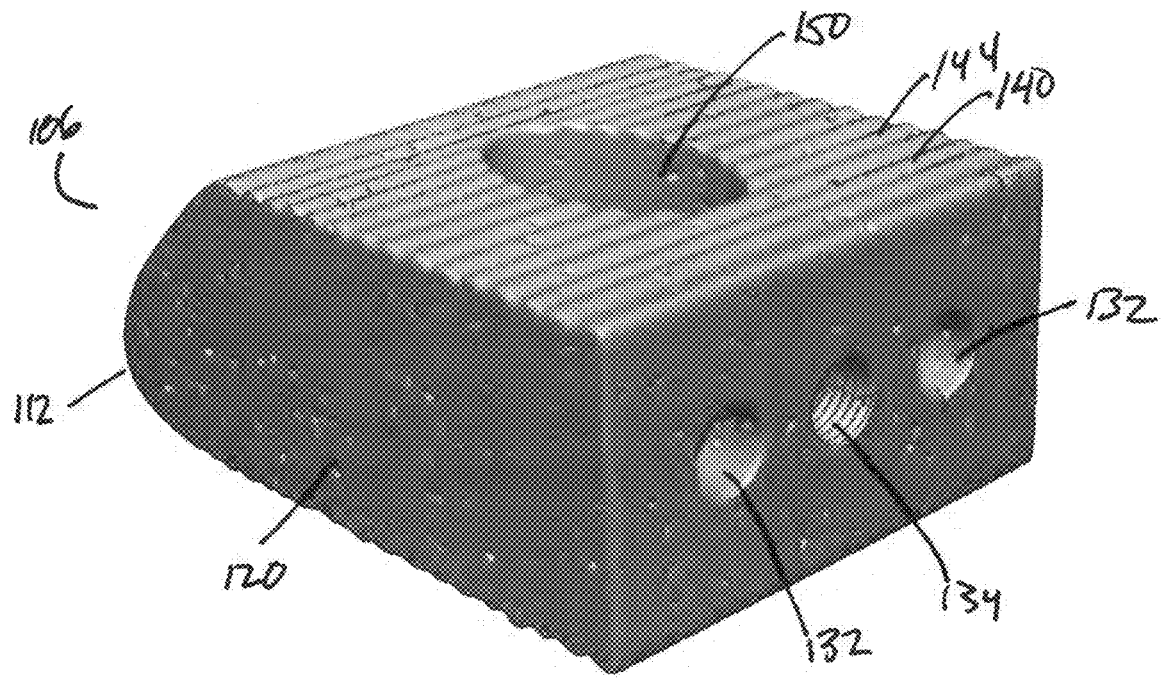
FIG. 4A is a perspective back view of an embodiment of the inventive implant with an off-centered nose and a graft window.
Figure 4B:
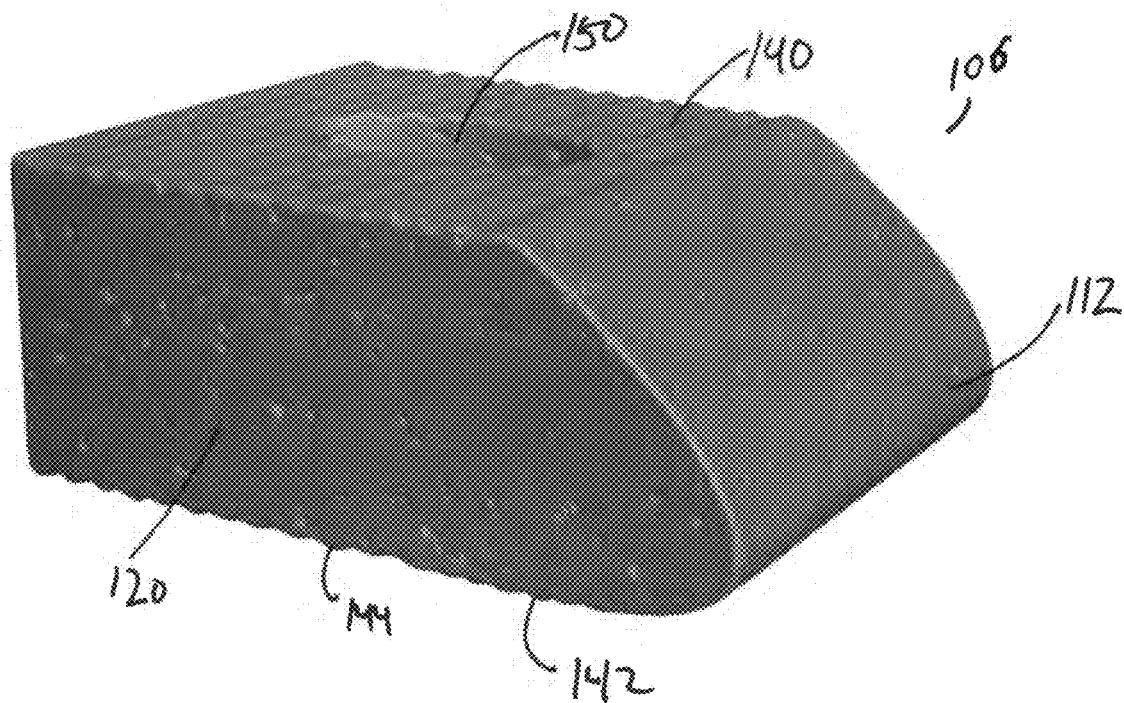
FIG. 4B is a front perspective view of the implant of figure of the inventive implant of FIG. 4A.

FIGS. 3A and 3B show embodiment 104, that is similar to embodiment 100, but with an offset blunt nose 112. FIGS. 4A and 4B show embodiment 106, which has the offset nose and the graft window 150. The blunt nose 112 in embodiments 104 and 106 is biased towards the inferior face of the implant. Put differently, the transverse axis used for the radius defining the curvature of the blunt nose is biased towards the inferior side of the implant. By contrast, the transverse axis used for the radius defining blunt nose 110 in embodiment 100, where blunt nose 110 is centered between the inferior and superior sides, is centered between the inferior and superior sides.

Thus, there are at least four embodiments of the shim of this invention: (1) centered blunt nose, no graft window (100); (2) centered blunt nose, with the graft window (102); (3) offset blunt nose, no graft window (104); (4) offset blunt nose, with the graft window (106). Other embodiments are possible and within the scope of this invention.

The inventive implants are shims that are inserted by distraction of the facet joints and inserted into position with appropriate tools. In an embodiment, the shims are inserted in between the two facets and within the facet joint. In contrast to the prior art devices discussed above, such as the CAVUX®, HONOUR® ORB, Valeo® II C, UNIFLEX® Cervical cages, the inventive implants have a serrated surface, porous structure of the material, features which allow osseous in-growth and better fixation of the implant and consecutively of the joints. An additional embodiment of the instant invention provides a graft window which allows osseous growth and may provide additional osseous integration.

In an embodiment, the entire implant is fabricated from medically compatible tantalum, titanium, tantalum alloy, or titanium alloy. For example, an appropriate titanium alloy may be titanium 6AL4V and 6AL4V ELI (ASTM Standard F1472, https://www.astm.org/Standards/F1472.htm (see also https://en.wikipedia.org/wiki/Ti-6Al-4V)), which are alloys made with about 6% aluminum and 4% vanadium. An appropriate tantalum alloy may be tantalum alloyed with 2.5% to 10% tungsten, or 40% niobium. These materials are known to have good biocompatibility and match the modulus of elasticity of bone. In an embodiment, the implant may be manufactured from a titanium alloy in accordance with ASTM F136, or where exterior surfaces are coated with medical-grade commercially pure titanium (CP Ti) per ASTM F1580.

In an embodiment, all surfaces of the implant may be roughened with macro surface roughness or nano-coating. This may be accomplished with a technique such as grit blasting, acid etching, or plasma spray coating (also called thermal spray coating).

In an embodiment, all surfaces of the implant are coated with hydroxyapatite (HA) and/or tricalcium phosphate (TCP), with a coating thickness of approximately 35 μm. HA and TCP are well known as osteoconductive materials that encourage bone growth.

In an embodiment, the implant may be fabricated from a porous material known to enhance bone in-growth, for example with pore sizes ranging in 200 to 900 μm to facilitate in-growth and have a porosity of 60-65% to mimic cancellous bone. The combination of surface roughness, HA or TCP coating, and porosity will facilitate in growth which is desirable for fusion.

The inventive shim implants of this invention may be implanted by known minimally invasive methods. For example, prior to inserting the shim implant, the patent may be positioned prone with face down and the adequate intra-operative imaging of the desired facet joint(s) is assessed. Then a paracentral stab incision is made in line with and caudal to the facet joint on the anterior-posterior projection, and a blunt entry dilator or chisel is guided through the soft tissues and is placed in between the facet joint. A subsequent dilator or series of dilators is then placed over the initial dilator and into the facet joint to access the joint space, and the blunt entry chisel or dilator is removed while the outer most dilator is kept in place. Subsequently, the extra-articular portion of the facet joint is decorticated with a decortication tool used first over and/or around the dilator, and a rasp next within the dilator to decorticate the intra-articular portion of the facet joint. Once decortication is complete, the shim implant is inserted under image guidance with a shim inserter device. After the shim implant is in position the shim inserter device is removed. Graft material can optionally be packaged posterior to and around the implant through the distractor tool. The dilator tool is then removed, and soft tissue closure and dressing are performed. In the detailed description below, the subsequent dilators are labeled as tongs.

Tools

In an embodiment, the implants herein may be implanted into a cervical facet joint in a posterior approach.

In an embodiment a series of nestable tools are provided to place the implants of this invention.

In an embodiment, an entry chisel 210 is provided as depicted in FIGS. 5A, 5B, and 5C, comprising a shaft having a distal and proximal end. The distal end is the tip of the chisel 211, with smooth inferior and superior surfaces. The proximal end 212 has a roughened surface. The device may have dual cannulation channels 214. The channels 214 may accept a guidewire to guide the placement of the apparatus as discussed herein. The device shaft may have rounded superior and inferior surfaces 218 and flat sides 219. The chisel has a uniform cross-sectional profile because in the next step, the first tong is inserted using the chisel as a guide (FIG. 7). The rounded superior and inferior surfaces and flat sides prevent the first tong from rotating out of plane from the chisel at the next step of the procedure. The chisel further has a series of transfer perforations (holes) 216 that serve as navigational landmarks for intra-operative imaging to evaluate the position of the tool during the implantation procedure.

Operationally, chisel 210 can be placed with the assistance of guide wires that fit within cannulation channels 214. This feature assists the accurate placement of the tool during surgery. The chisel position can also be modified with the use of such guide wires.

FIGS. 6A-6D depict a first tong 230 that entry chisel 210 nestles within. The distal end of the first tong 230 has two prongs 234 that may be smooth or roughened. The proximal end has roughened surface 235 for ease of manual manipulation by the surgeon. A central channel 232 runs the entire length of the tong 230. The profile (i.e., cross section) of channel 232 matches the cross section of entry chisel 210. The rounded superior and inferior surfaces 218 along the shaft, and flattened sides 219 of the chisel shaft ensure rotational stability when the chisel is inserted into channel 232. The tong includes holes 236 for intraoperative imaging of the position of the tool. Because first tong 230 may nestle within a second tong (FIG. 11), tong 230 has a uniform cross-sectional profile with rounded top and bottom 238 and flattened sides 239. Tong 230 may also be equipped with attachment point 237 providing a firm connection handle 270 (FIG. 9).

The embedding of chisel 210 within tong 230 is shown in FIGS. 7A-7D. FIGS. 7A and 7B are two perspective views of the entire tool, viewed from the distal end (FIG. 7A) and proximal end (FIG. 7B). Details of the distal end 242 are shown in FIG. 7C and proximal end 244 are shown in FIG. 7D. In the distal end 242, chisel tip 211 is flush with prongs 234. Proximal end 244 shows the proximal end 212 of entry chisel 210 nested within the channel of tong 230. Proximal end 212 juts beyond the roughened proximal end 235 of tong 230.

The next step in the procedure relies on a first decorticator 250 (FIGS. 8A-8D). FIG. 8A is a perspective view from the distal end, and FIG. 8B is a perspective of the entire tool from the proximal end. FIG. 8C is a close up of the distal end 255 of decorticator 250 showing additional detail. FIG. 8D is a close-up of proximal end 253 of decorticator 250 showing additional detail. Decorticator 250 is a round hollow shaft (251) running the length of the tool except for the proximal region 258. Shaft 251 defines channel 252 that runs the length of the tool. The distal end 255 has a diagonal cut forming an ellipsis 254 around the distal end of channel 252. The inferior edge of the distal end of decorticator 250 is jagged with teeth 256. The proximal end is depicted with octagonal cross section 258. Other shapes (besides octagonal) for 258 are possible, such as hexagonal or others. The proximal terminus of channel 252 is shown in FIG. 8D. Also shown are anchor points 259 for connection to handle 270 (FIG. 9).

As shown in FIGS. 9A-9C, the chisel nested in tong 230 depicted in FIG. 7 is inserted into channel 252 of decorticator 250. Handle 270 may be placed over decorticator 250 to provide a firm grip for the surgeon to manipulate decorticator or other instruments into position. In the illustrated embodiment, handle 270 includes features such as protuberance 271 to improve the grip of the surgeon. Also shown is collar 272 to assist in securing handle 270 to decorticator 250. The handle may nest over octagonal section 258 on the decorticator. There may also be a mechanism that interacts with holes 259 and 237 to secure handle 270 on decorticator 250.

The decortication procedure involves removal of superficial bone and other tissue to prepare a site for bone grafting for the purpose of fusing of the vertebrae or facet joint. When the degree of desired tissue removal is achieved, the decorticator is removed. If additional decortication is needed additional tongs can be layered over the first tong as discussed in the following paragraphs.

As shown in FIGS. 10A-10C, a second facet tong 280 may be provided, having a distal end with two prongs 284 that may be smooth or roughened and a proximal end with roughened surface 285. Tong 280 has shaft 281 running the entire length of the tool. Within shaft 281 is channel 282, adapted to accept tong 230 within it. Accordingly, the upper and lower surfaces of channel 282 are rounded and the sides are flat, to accommodate the cross-sectional profile of tong 230. On tong 280, the superior and inferior surfaces 288 are rounded, and sides 289 are flat. Also provided is handle attachment point 287 and a series of transverse perforations 286 for intraoperative imaging of the position of the tool.

FIGS. 11A-11D show the apparatus of FIG. 7 inserted into second tong 280. Thus, 294 (FIG. 11C) shows the distal end of this arrangement, with entry chisel 210 nested within first tong 230 and nested within second tong 280. FIG. 11C shows flattened chisel tip 211 flush with prongs 234 (from tong 230) and 284 (from tong 280). The proximal end of this arrangement is shown in FIG. 11D, which depicts chisel proximal end 212 nested within first tong proximal end 236 and nested within second tong proximal end 285.

FIGS. 12A and 12B show a second decorticator 310 that is similar to decorticator 250 only larger to accommodate the apparatus as depicted in FIG. 11 within it. FIG. 12A is a perspective view from the distal end, and FIG. 12B is a perspective of the entire tool from the proximal end. Decorticator 311 comprises a hollow round (in cross-section) shaft 311 that runs the entire length of the tool. This shaft is designed to fit entry chisel 210 nested within first tong 230 and nested within second tong 280 shown in FIG. 11 within it (shown in FIG. 13). Distal end 313 of decorticator 310 has an inferior edge 316 with jagged teeth for decorticating bone. Also depicted is a diagonal cut at the distal end to make ellipsis 314. The proximal end 318 of decorticator 310 is depicted with an octagonal cross section. Other shapes (besides octagonal) for 318 are possible, such as hexagonal or others. The proximal terminus of channel 312 is shown in FIG. 12B. Also shown are anchor points 319 for connection to handle 330 (FIG. 13A).

The apparatus of FIG. 11 is nested within 312 as shown in FIGS. 13A-13C. FIG. 13C is a detail view of distal end of decorticator 310 with entry chisel 210 nested within first tong 230 and nested within second tong 280 (294) inserted within channel 312 in the operational position. Handle 330 is than affixed to the proximal end of decorticator 310 as shown. A mechanism is provided to securely affix handle 330 to the decorticator without allowing the nested chisel and tongs 294 to move. Also shown is collar 332 to assist in securing handle 330 to decorticator 310.

Operationally, the apparatus of FIG. 13 is used to decorticate and roughen the bone surfaces on the joint as discussed above. Decorticator 2 is then removed, leaving apparatus 294 in the joint. If additional distraction or access to a larger surface area is desired, a third tong 340 may be employed, shown in FIGS. 14A-14C. Tong 340 is similar to tongs 280 and 230 but is larger to accommodate the apparatus of FIG. 11 within. Thus, tong 340 has shaft 341 and channel 342 running the entire length of the tool. The distal end of tong 340 has two prongs 344 that may be smooth or roughened. The proximal end has a roughened outer surface 345. It can be seen is FIG. 14C showing detail of the proximal end, that channel 342 has an interior cross-section matching the cross-section of the exterior of second prong 280. Also shown is anchor point 347 for a handle, and series of transverse perforations 346 for intra-operative imaging to evaluate position of the tool.

FIG. 15 shows the apparatus of FIG. 11 inserted into channel 342. FIG. 15A is a perspective view of the entire tool from the distal end. FIG. 15B is a perspective view of the entire tool from the proximal end. FIG. 15C is a detail view of distal end, showing the entry chisel 210, first tong 230, second tong 280, and third tong 340 nested together, with each of prongs 234, 284, and 344 flush with chisel tip 211. The proximal end of this arrangement is shown in FIG. 15D, with each of 212, 235 and 285 nested together and within channel 342.

Operational, the apparatus of FIG. 15 is now wedged within the facet joint at the desired position. At this stage the chisel, first tong, and second tong are removed as follows.

First, as depicted in FIGS. 16A-16C, chisel 210 is withdrawn from the apparatus of FIG. 15. This can be seen clearly in the detail of FIG. 16C, showing distal end 353 with channel 232 in facet tong 230 empty. This can also be seen at the proximal end 354 in FIG. 16B, where the proximal end 212 of chisel 210 is absent. Next, first facet tong 230 is withdrawn to give the apparatus shown in FIGS. 17A and 17B. Finally, second facet tong 280 is withdrawn to give the appearance shown in FIGS. 18A and 18B. At this stage prongs 344 are embedded in the facet joint.

Thus, the entry chisel 210 and first, second, and third tongs decorticate and establish the appropriate width for the implants as described herein. As discussed in the following paragraphs, the height of the distraction for the implant is established with one or more rasps.

Accordingly, as shown in FIGS. 19A-19C and FIGS. 20-20A, rasp 400 is inserted into facet tong 340. Rasps of various sizes, as discussed herein, are used to further decorticate the facet joint in preparation of placement of implant. Rasp 400 is illustrated with several views in FIGS. 19A-19C. The rasp has a shank 402 running the length from the rasp head at the distal end to the handle at the proximal end. As illustrated, the shank as a rectangular cross-sectional profile. The rasp head has a roughened superior surface 412 and a roughened inferior surface 414, a distal tip 410 and an angled leading edge 416. The proximal end of rasp 400 is a handle 418 to aid in insertion and removal.

Rasp 400 is inserted into fact tong 340 as shown in FIGS. 20A and 20B. The head of the rasp (i.e., 416) is flush with fork prongs 344. Shank 402 is sized to that handle 418 fits over the proximal end of facet tong 340.

The rasp head may be made available in a variety of heights and widths. In terms of width, this rasp can be sized to fit into facet tong 230 or 280 or 340. The height of the rasp head is function of the requirements of the surgery to adjust the facet joint for the desired height of the implant.

This procedure may only need a smaller size and can rely on a rasp inserted into facet tong 230 or 280. Similarly, this procedure may only need a smaller implant that would match the rasp. For illustrative purposes, the remainder of the procedure is illustrated with facet tong 340. Rasps intended for tongs 230 or 280 must have a length appropriate to the tong tool.

The next step is insertion of an implant into facet tong 340. The implant is attached to implant inserter 430 (FIGS. 21A and 21B). Inserter 430 has shaft 432 running the length of the tool. Head 433 is at the distal end. In the illustrated embodiment, the distal end has dual prongs 434 to match the implants (FIGS. 1-4) and a central threaded head 436 to firmly affix the implant to the tool. The threaded head has male threads and is rotated by handle 438 on the proximal end of inserter 430. An internal axle 435 (not shown) links handle 438 to threaded head 436 to screw the implant onto or off the tool. Also shown in FIG. 21A is marker 437 near the proximal end to indicate the implant is flush with facet tongs distally. Only one such marking is shown but multiple markings may be employed to match various facet tongs.

In an embodiment, the implant affixed to inserter tool 430 is shown in FIGS. 22A, 22B and 23. Implant 106 is illustrated. To affix the implant to the inserter, male threads 436 are inserted into female threads 134 (FIGS. 1-4) and screwed into place by rotating knob 438. Prongs 434 are aligned with indents 132 on the implant and male thread 436 are turned all the way to affix implant 106 to inserter 430. FIG. 23 is a cutaway view of an embodiment of the implant affixed to the inserter tool with male threads 436 and dual prongs 434.

The implant affixed to the inserter tool is then inserted into facet tong 340 as shown in FIGS. 24A-24C. The implant is inserted into position and inserter tool 430 is removed by unscrewing the tool from the implant by turning knob 438. Additional graft material may be placed through facet tong to aid in fusion. The facet tong 340 is removed leaving the implant in position and the surgery is completed.

Thus, the nested series of tongs adjusts the width of the space in the facet joint for the implant such as 100, 102, 104, or 106, and rasps 400 can be produced in various heights to establish the height of the space for the implant. For example, if a narrower width is sufficient, the surgeon may only require the first and second tongs and omit the third tong. Similarly, if the anatomical requirements are for an even wider implant, a fourth or even fifth tong can be employed.

Drawings Legend

| No. | Description |
|---|---|
| 100 | Inventive implant, centered blunt nose, no graft window |
| 102 | Inventive implant, centered blunt nose, with graft window |
| 104 | Inventive implant, offset blunt nose, no graft window |
| 106 | Inventive implant, offset blunt nose, with graft window |
| 110 | Centered Blunt nose |
| 112 | Offset blunt nose |
| 120 | Side face |
| 130 | Proximal face |
| 132 | insertion device engagement indent |
| 134 | insertion device engagement indent with threads |
| 140 | Superior face |
| 142 | Inferior face |
| 144 | Serrations in superior and inferior faces |
| 146 | Pores in surface |
| 150 | Graft window |
| 200 | Tool system |
| 210 | Entry chisel |
| 211 | Flattened smooth Chisel tip, distal end |
| 212 | Roughened proximal end |
| 214 | Cannulations for guidewires (dual) |
| 216 | Holes in chisel (markers) for intra-operative imaging to evaluate position of the tool |
| 218 | Rounded top and bottom |
| 219 | Flattened sides |
| 230 | Facet tong 1 |
| 231 | Facet tong 1 shaft |
| 232 | Hollow channel in tong |
| 234 | Fork prong (dual) |
| 235 | Roughened proximal end |
| 236 | Holes in shaft for intra-operative imaging to evaluate position of the tool |
| 237 | removable handle attachment point |
| 238 | Rounded top and bottom |
| 239 | Flattened sides |
| 240 | Entry chisel nested inside facet tong 1 |
| 242 | Distal end of Entry chisel nested inside facet tong 1 |
| 244 | Proximal end of Entry chisel nested inside facet tong 1 |
| 250 | Decorticator 1 |
| 251 | Decorticator hollow shaft |
| 252 | Central hollow channel, cannulation to fit over tong 1 |
| 253 | Decorticator proximal end |
| 254 | distal end elliptical shape |
| 255 | Decorticator distal end |
| 256 | Distal end with jagged teeth |
| 258 | Proximal end with octagonal cross section |
| 259 | Holes in proximal end for anchoring with tool 270 |
| 270 | Handle |
| 271 | Grip protuberance |
| 272 | Handle collar |
| 274 | Chisel and tong 1 nested inside decorticator |
| 280 | Facet tong 2 |
| 281 | Facet tong 2 shaft |
| 282 | Channel to fit over facet tong 1 |
| 284 | Fork prong in tong 2 (dual) |
| 285 | Roughened proximal end |
| 286 | Holes in shaft |
| 287 | removable handle attachment point |
| 288 | Rounded superior and inferior surfaces |
| 289 | Flat sides |
| 294 | Chisel nested in tong 1 nested in tong 2 distal end |
| 296 | Chisel nested in tong 1 nested in tong 2 proximal end |
| 310 | Decorticator 2 |

Drawings Legend -continued

| No. | Description |
|---|---|
| 311 | Decorticator 2 shaft |
| 312 | Central hollow channel, cannulation to fit over tong 2 |
| 313 | Distal end of decorticator 2 |
| 314 | distal end elliptical shape Decorticator 2 |
| 316 | Distal end with jagged teeth Decorticator 2 |
| 318 | Proximal end with octagonal cross section Decorticator 2 |
| 319 | Holes in proximal end for anchoring with tool 270 Decorticator 2 |
| 330 | Handle for decorticator 2 |
| 332 | Collar for Handle for decorticator 2 |
| 334 | Chisel, tong 1, decorticator 1, tong 2 nested in decorticator 2 |
| 340 | Facet tong 3 |
| 341 | Facet tong 3 shaft |
| 342 | Channel to fit over facet tong 2 |
| 344 | Fork prong in tong 3 (dual) |
| 345 | Roughened distal end tong 3 |
| 346 | Holes in tong 3 shaft |
| 347 | Holes in distal end |
| 348 | Flat internal sides of tong 3 channel |
| 349 | Rounded top and bottom interior surfaces of tong 3 channel |
| 351 | Chisel, tong 1, tong 2 tong 3 nested together distal tip |
| 353 | Distal tip of 351 but with chisel removed. tong 1, tong 2 tong 3 nested together |
| 354 | Proximal end of tong 1, tong 2, tong 3 nested together |
| 355 | Distal tip of 351 with chisel and tong 1 removed, tong 2, tong 3 nested together |
| 356 | Proximal end of tong 2, tong 3 nested together |
| 400 | rasp |
| 402 | Rasp shank |
| 410 | Rasp distal end |
| 412 | Rasp roughened superior end surface |
| 414 | Rasp roughened inferior end surface |
| 416 | Rasp angled leading edge |
| 418 | Rasp handle |
| 420 | Rasp nested in tong 3 |
| 430 | Implant inserter |
| 432 | Implant inserter shaft |
| 433 | Implant inserter distal end |
| 434 | Outer Implant prong (dual) |
| 435 | Implant inner shaft (not shown) |
| 436 | Central implant prong threaded |
| 437 | Markings on shaft proximally to indicate the implant is flush with facet tongs distally (only one such marking is drawn but multiple markings would be employed to match various facet tongs) |
| 438 | Handle to unscrew central prong |
| 439 | Roughened distal end |
| 440 | Implant inserter nested in tong 3 |
| 442 | Distal end of Implant inserter nested in tong 3 |
| 444 | Proximal end of Implant inserter nested in tong 3 |

The invention claimed is:

1. A shim implant for the fusion of a cervical facet joint, comprising a generally rounded or box-shaped body having a distal face, a proximal face, superior and inferior surfaces in a generally parallel orientation, and two side faces in a generally parallel orientation, wherein a transverse axis can be defined as a line perpendicular to the side faces,
   a. wherein the distal face has a rounded profile defined by an arc having a radius on a transverse axis, wherein the proximal face has one or more insertion device engagement features;
   b. wherein the superior and inferior surfaces each comprise serrations with a plurality of grooves on a transverse axis generally spanning the entire length of a transverse axis;

c. wherein the implant is fabricated from titanium metal or alloy or tantalum metal or alloy, and has a roughened surface, and all surfaces of the implant are coated with hydroxyapatite or tri-calcium phosphate or both and wherein the implant is porous to allow for bone in-growth; and d. wherein the hydroxyapatite or tri-calcium phosphate coating has a thickness of approximately 35 μm.

2. The implant of claim 1, wherein the implant further comprises a graft window comprising a perforation spanning the distance between the superior and inferior surfaces.

3. The implant of claim 1 wherein the rounded profile of the distal face is biased towards the inferior surface.

4. The implant of claim 1, wherein the insertion device engagement features comprise one or more holes in the proximal face.

5. The insertion device engagement features of claim 4, further comprising three holes aligned on a transverse axis on the proximal face.

6. The insertion engagement feature of claim 5, wherein the central hole comprises female screw threads for engaging a male threaded tool.

7. The insertion engagement feature of claim 4, wherein at least one hole comprises female screw threads for engaging a male threaded tool.

8. The implant of claim 1, wherein each surface is roughened with a macro surface roughener or nano-coating.

9. The implant of claim 1, wherein the porous material has pore sizes ranging in 200 to 900 μm.

10. A method for treating stenosis with or without radiculopathy comprising surgical distraction of the relevant cervical vertebrae and insertion of the implant of claim 1.

* * * * *